US010610587B2

(12) United States Patent
Chang et al.

(10) Patent No.: US 10,610,587 B2
(45) Date of Patent: Apr. 7, 2020

(54) ADJUVANT COMPOSITION CONTAINING AT LEAST ONE INFLUENZA VIRUS NEUTRALIZING AND BINDING MOLECULE AND VACCINE COMPOSITION CONTAINING SAME

(71) Applicant: CELLTRION INC., Incheon (KR)

(72) Inventors: Shin Jae Chang, Incheon (KR); Soo Young Lee, Incheon (KR); Byung Pil Lim, Seoul (KR); Pan Kyeom Kim, Incheon (KR); Sang Tae Park, Incheon (KR); Jung Sun Ahn, Incheon (KR); Eun Bee Park, Seoul (KR); Sun Ju Keum, Incheon (KR); Man Ki Song, Seoul (KR); Jung Ah Choi, Seoul (KR)

(73) Assignee: CELLTRION INC., Incheon (KR)

( * ) Notice: Subject to any disclaimer, the term of this patent is extended or adjusted under 35 U.S.C. 154(b) by 0 days.

(21) Appl. No.: 16/130,405

(22) Filed: Sep. 13, 2018

(65) Prior Publication Data

US 2019/0000968 A1  Jan. 3, 2019

Related U.S. Application Data

(62) Division of application No. 15/533,269, filed as application No. PCT/KR2015/013279 on May 12, 2015, now abandoned.

(30) Foreign Application Priority Data

Dec. 5, 2014  (KR) .................. 10-2014-0173469
Aug. 11, 2015  (KR) .................. 10-2015-0113515

(51) Int. Cl.
*A61K 39/39* (2006.01)
*A61K 39/145* (2006.01)
*C07K 16/00* (2006.01)
*A61K 39/395* (2006.01)
*A61K 39/42* (2006.01)
*C07K 16/10* (2006.01)
*C12N 7/00* (2006.01)
*A61K 39/00* (2006.01)

(52) U.S. Cl.
CPC ............ *A61K 39/39* (2013.01); *A61K 39/145* (2013.01); *A61K 39/395* (2013.01); *A61K 39/42* (2013.01); *C07K 16/00* (2013.01); *C07K 16/1018* (2013.01); *C12N 7/00* (2013.01); *A61K 2039/505* (2013.01); *A61K 2039/55516* (2013.01); *A61K 2039/575* (2013.01); *C07K 2317/565* (2013.01); *C12N 2760/16134* (2013.01); *C12N 2760/16171* (2013.01)

(58) Field of Classification Search
None
See application file for complete search history.

(56) References Cited

U.S. PATENT DOCUMENTS

| 9,573,991 | B2* | 2/2017 | Chang | ................ C07K 16/1018 |
| 2008/0311135 | A1* | 12/2008 | Zheng | .................. A61K 39/39 |
| | | | | 424/178.1 |
| 2010/0040635 | A1 | 2/2010 | Horowitz et al. | |
| 2013/0004505 | A1 | 1/2013 | Chang et al. | |
| 2014/0234336 | A1 | 8/2014 | Chang et al. | |
| 2016/0052997 | A1 | 2/2016 | Hong et al. | |
| 2018/0008702 | A1 | 1/2018 | Chang et al. | |

FOREIGN PATENT DOCUMENTS

| KR | 10-2004-0067687 A | 7/2004 |
| KR | 10-2011-0047193 A | 5/2011 |
| KR | 10-2011-0102198 A | 9/2011 |
| KR | 10-2013-0035916 A | 4/2013 |
| KR | 10-2014-0119641 A | 10/2014 |
| WO | WO 2009/036157 A1 | 3/2009 |

OTHER PUBLICATIONS

Okuno et al. A Common Neutralizing Epitope Conserved between the Hemagglutinins of Influenza A Virus Hi and H2 Strains. Journal of Virology, May 1993, p. 2552-2558, vol. 67, No. 5.*
International Search Report in connection with PCT International Application No. PCT/KR2015/013279 including English language translation.
John Treanor, M.D., "Influenza Vaccine—Outmaneuvering Antigenic Shift and Drift," The New England Journal of Medicine, 2004.
Timothy K. W. Cheung et al., "Biology of Influenza A Virus," Ann. N.Y. Acad. Sci., 2007.
Suxiang Tong et al., "A distinct lineage of influenza A virus from bats," PNAS, 2012.
Rino Rappuoli et al., "Vaccines for the twenty-first century society," Nature Reviews, 2011.
Supplementary Partial European Search Report dated Oct. 2, 2017 by the European Patent Office in connection with related European Application No. EP 15 86 6215.
Jose F. Ponte et al., "Enhancement of humoral and cellular immunity with an antiglucocorticoid-induced tumour necrosis factor receptor monoclonal antibody", Immunology, 2010, 130, pp. 231-242.

(Continued)

*Primary Examiner* — Nianxiang Zou
(74) *Attorney, Agent, or Firm* — John P. White; Cooper & Dunham LLP

(57) ABSTRACT

This invention relates to an adjuvant composition containing at least one binding molecule for neutralizing influenza virus and a vaccine composition containing the same. The composition containing at least one binding molecule for neutralizing influenza virus is capable of increasing the effects of a vaccine, and can thus be used as an adjuvant, which increases an immune response upon vaccine administration, and is very useful in the prevention of diseases caused by viruses.

4 Claims, 14 Drawing Sheets

Specification includes a Sequence Listing.

(56) References Cited

OTHER PUBLICATIONS

Dreyfus et al. "Structure of a Classical Broadly Neutralizing Stem Antibody in Complex with a Pandemic H2 Influenza Virus Hemagglutinin", *Journal of Virology*, 2013, 87:7149-7154.

* cited by examiner

SEQUENCE LISTING

```
<160> NUMBER OF SEQ ID NOS: 16

<210> SEQ ID NO 1
<211> LENGTH: 11
<212> TYPE: PRT
<213> ORGANISM: Artificial Sequence
<220> FEATURE:
<223> OTHER INFORMATION: CT120 light chain CDR1

<400> SEQUENCE: 1

Arg Ala Ser Glu Asn Ile Trp Asn Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CT120 light chain CDR2

<400> SEQUENCE: 2

Gly Ala Ser Thr Gly Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CT120 light chain CDR3

<400> SEQUENCE: 3

Gln Gln Tyr Asn Ser Trp Pro Arg Thr
1               5

<210> SEQ ID NO 4
<211> LENGTH: 5
<212> TYPE: PRT
<213> ORGANISM: Artificial Sequence
<220> FEATURE:
<223> OTHER INFORMATION: CT120 heavy chain CDR1

<400> SEQUENCE: 4

Ser His Ala Ile Ser
1               5

<210> SEQ ID NO 5
<211> LENGTH: 17
<212> TYPE: PRT
<213> ORGANISM: Artificial Sequence
<220> FEATURE:
<223> OTHER INFORMATION: CT120 heavy chain CDR2

<400> SEQUENCE: 5

Gly Ile Ser Pro Met Phe Gly Thr Thr His Tyr Ala Gln Lys Phe Gln
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: CT120 heavy chain CDR3

<400> SEQUENCE: 6
```

Asp Gly Ala Gly Ser Tyr Tyr Pro Leu Asn Trp Phe Asp Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: CT149 light chain CDR1

<400> SEQUENCE: 7

Arg Ala Ser His Arg Val Gly Ser Thr Tyr Ile Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CT149 light chain CDR2

<400> SEQUENCE: 8

Gly Ala Ser Asn Arg Ala Thr
1               5

<210> SEQ ID NO 9
<211> LENGTH: 9
<212> TYPE: PRT
<213> ORGANISM: Artificial Sequence
<220> FEATURE:
<223> OTHER INFORMATION: CT149 light chain CDR3

<400> SEQUENCE: 9

Gln Gln Phe Ser Val Ser Pro Trp Thr
1               5

<210> SEQ ID NO 10
<211> LENGTH: 5
<212> TYPE: PRT
<213> ORGANISM: Artificial Sequence
<220> FEATURE:
<223> OTHER INFORMATION: CT149 heavy chain CDR1

<400> SEQUENCE: 10

Thr Tyr Gly Val Ser
1               5

<210> SEQ ID NO 11
<211> LENGTH: 17
<212> TYPE: PRT
<213> ORGANISM: Artificial Sequence
<220> FEATURE:
<223> OTHER INFORMATION: CT149 heavy chain CDR2

<400> SEQUENCE: 11

Trp Ile Ser Ala Tyr Thr Gly Ile Thr Asp Tyr Ala Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: CT149 heavy chain CDR3

<400> SEQUENCE: 12

```
Asp Lys Val Gln Gly Arg Val Glu Val Gly Ser Gly Arg His Asp
1               5                   10                  15

Tyr

<210> SEQ ID NO 13
<211> LENGTH: 234
<212> TYPE: PRT
<213> ORGANISM: Artificial Sequence
<220> FEATURE:
<223> OTHER INFORMATION: CT120 light chain

<400> SEQUENCE: 13

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Glu Asn
            35                  40                  45

Ile Trp Asn Asn Leu Ala Trp Tyr Gln Gln Lys Pro Gly Gln Ala Pro
    50                  55                  60

Arg Leu Leu Ile Ser Gly Ala Ser Thr Gly Ala Thr Gly Val Pro Ser
65                  70                  75                  80

Arg Phe Arg Gly Ser Gly Ser Arg Thr Glu Phe Thr Leu Thr Ile Ser
                85                  90                  95

Ser Leu Gln Ser Glu Asp Phe Ala Ile Tyr Phe Cys Gln Gln Tyr Asn
                100                 105                 110

Ser Trp Pro Arg Thr Phe Gly Pro Gly Thr Lys Val Glu Ile Lys Arg
            115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 14
<211> LENGTH: 472
<212> TYPE: PRT
<213> ORGANISM: Artificial Sequence
<220> FEATURE:
<223> OTHER INFORMATION: CT120 heavy chain

<400> SEQUENCE: 14

Met Asp Trp Thr Trp Arg Phe Leu Phe Val Val Ala Ala Ala Thr Gly
1               5                   10                  15

Val Gln Cys Gln Val Gln Leu Val Gln Ser Gly Ala Glu Val Lys Met
                20                  25                  30

Pro Gly Ser Ser Val Lys Val Ser Cys Lys Thr Ser Gly Val Phe Phe
            35                  40                  45
```

```
Ser Ser His Ala Ile Ser Trp Val Arg Gln Ala Pro Gly Gln Gly Leu
    50              55                  60

Glu Trp Met Gly Gly Ile Ser Pro Met Phe Gly Thr Thr His Tyr Ala
65              70                  75                  80

Gln Lys Phe Gln Gly Arg Val Thr Ile Thr Ala Asp Gln Ser Thr Thr
                85                  90                  95

Thr Ala Tyr Met Glu Leu Thr Ser Leu Thr Ser Glu Asp Thr Ala Val
            100                 105                 110

Tyr Tyr Cys Ala Arg Asp Gly Ala Gly Ser Tyr Tyr Pro Leu Asn Trp
        115                 120                 125

Phe Asp Pro Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Arg Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Gly Leu His Asn His Tyr Thr Gln Lys
    450                 455                 460
```

Ser Leu Ser Leu Phe Pro Gly Lys
465                 470

<210> SEQ ID NO 15
<211> LENGTH: 215
<212> TYPE: PRT
<213> ORGANISM: Artificial Sequence
<220> FEATURE:
<223> OTHER INFORMATION: CT149 light chain

<400> SEQUENCE: 15

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Arg Val Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 16
<211> LENGTH: 456
<212> TYPE: PRT
<213> ORGANISM: Artificial Sequence
<220> FEATURE:
<223> OTHER INFORMATION: CT149 heavy chain

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Pro Glu Trp Val
        35                  40                  45

Gly Trp Ile Ser Ala Tyr Thr Gly Ile Thr Asp Tyr Ala Gln Lys Phe
    50                  55                  60

Gln Gly Arg Val Thr Leu Thr Thr Asp Ala Thr Thr Ala Thr Ala Phe
65                  70                  75                  80

```
Leu Asp Leu Arg Ser Leu Arg Pro Asp Asp Thr Ala Thr Tyr Phe Cys
             85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Gly Leu His Asn His Tyr Thr Gln Lys
        435                 440                 445

Ser Leu Ser Leu Ser Pro Gly Lys
    450                 455
```

ADJUVANT COMPOSITION CONTAINING AT LEAST ONE INFLUENZA VIRUS NEUTRALIZING AND BINDING MOLECULE AND VACCINE COMPOSITION CONTAINING SAME

CROSS-REFERENCE TO RELATED APPLICATIONS

This application is a § 371 national stage of PCT International Application No. PCT/KR2015/013279, filed Dec. 5, 2015, claiming priority of Korean Patent Applications Nos. KR 10-2015-0113515, filed Aug. 11, 2015 and KR 10-2014-0173469, filed Dec. 5, 2014 the contents of each of which are hereby incorporated by reference into the application.

REFERENCE TO A SEQUENCE LISTING

This application incorporates-by-reference nucleotide and/or amino acid sequences which are present in the file named "180913_89708-Z_Sequence_Listing_CAE.txt", which is 14.8 kilobytes in size, and which was created Sep. 13, 2018 in the IBM-PC machine format, having an operating system compatibility with MS-Windows, which is Contained in the text file filed Sep. 13, 2018 as part of this application

TECHNICAL FIELD

The present invention relates to an adjuvant composition comprising at least one binding molecule for neutralizing influenza virus and a vaccine composition comprising the same, and more particularly to an adjuvant composition including at least one human monoclonal antibody having neutralizing activity against influenza virus, which functions as an adjuvant for enhancing an immune response induced by a vaccine to thus increase the efficacy of the vaccine, and to a vaccine composition comprising the same.

BACKGROUND ART

Influenza, which is an illness caused by infecting the respiratory tract with an influenza virus, is common in the winter and is highly infectious and easily spread to all ages, and is also known to particularly afflict the elderly (Treanor J, 2004, *N Engl. J* Med. 350(3):218-20). Influenza viruses, which are enveloped viruses belonging to the Orthomyxoviridae family and the genome of which consists of eight negative-sense single-stranded RNA (ribonucleic acid) segments, are classified into groups A, B and C, and influenza A viruses are further divided into a number of subtypes depending on HA (hemagglutinin) and NA (neuraminidase) as the major surface proteins. 17 types of HA and 10 types of NA are known so far (Cheung T K and Poon L L 2007, *Ann N Y* Acad. Sci. 1102:1-25; Tong S, et al. 2012, Proc. Natl. Acad. Sci. U.S.A. 109:4269-4274). Influenza viruses continuously produce variant viruses to thus features that may infect birds, pigs and humans depending on the types thereof and create a variety of gene combinations and mutations due to the genome comprising RNA segments. Treanor J, 2004. *N Engl. J Med.* 350(3):218-20). Because of such persistent mutations, it is difficult to obtain permanent immunity, and currently, the most effective prevention method is to form immunity appropriate for a particular type annually by inoculating a vaccine against influenza virus, which is predicted to be popular every year.

The influenza virus vaccine, which is currently inoculated every year, is a trivalent or tetravalent vaccine composed of HA of H1 and H3 subtypes of influenza A and one or two kinds of HA of influenza B.

A vaccine against various infectious diseases, including the influenza virus vaccine, may be added with a substance for increasing immunogenicity, and such a substance is referred to as an adjuvant. Examples of adjuvants approved for use on humans may include Alum, composed of aluminum hydroxide and aluminum phosphate, an oil-in-water emulsion MF59, AS03, and AS04, composed of the TLR4 agonist MPL and aluminum hydroxide (Rappuoli R, 2011. *Nature Reviews Immunology* 11, 11(12):865-72).

In addition thereto, there are many reports on enhancing an immune response by administering an antibody and an antigen together, and many attempts are being made to use the antibody as the adjuvant.

The antibody against influenza A virus, filed by the present applicant, exhibits neutralizing activity against various influenza subtypes, and particularly, the antibody disclosed in Korean Patent Application No. 10-2011-0020061 mainly shows neutralizing activity against phylogenetic group 1 (H1, H2, H5, H9, etc.) and the antibody disclosed in Korean Patent Application No. 10-2012-0107512 mainly shows neutralizing activity against phylogenetic group 2 (H3, H7, etc.). Hence, there has been developed a cocktail formulation, which is configured such that two or more kinds of antibodies are mixed and co-administered to thereby exhibit preventive and therapeutic effects against viruses of Groups 1 and 2, which are likely to become pandemic, as disclosed in Korean Patent Application No. 10-2014-0036601.

DISCLOSURE

Technical Problem

The present inventors have ascertained that the effect of a vaccine may be increased by administering the vaccine together with the antibody for neutralizing influenza virus, which was already developed by the present inventors, and have found the new use of the already-developed antibody as the adjuvant, thus culminating in the present invention.

Accordingly, the present invention is intended to provide an adjuvant composition comprising at least one binding molecule for neutralizing influenza virus.

In addition, the present invention is intended to provide a vaccine composition comprising the adjuvant composition and a target antigen.

In addition, the present invention is intended to provide a method of producing the vaccine composition comprising the adjuvant composition and the target antigen.

In addition, the present invention is intended to provide a method of increasing an immune response to a target antigen by administering the adjuvant composition to a host.

In addition, the present invention is intended to provide a method of immunizing a host by administering the vaccine composition to the host.

In addition, the present invention is intended to provide a method of preparing an immunological product from the host immunized by administering the vaccine composition to the host.

Technical Solution

Therefore, the present invention provides an adjuvant composition comprising at least one binding molecule for neutralizing influenza virus.

In an embodiment of the present invention, the binding molecule may bind to an epitope in a stem region of a hemagglutinin (HA) protein of influenza A virus.

In an embodiment of the present invention, the epitope of the binding molecule may be at least one selected from the group consisting of i) an epitope comprising any one amino acid residue selected from the group consisting of amino acids at positions 18, 25, 27, 32, 33, 38, 40, 54, 55, 278, 291, 292, 310, 311, 312 and 318 of an HA1 polypeptide; and ii) an epitope comprising any one amino acid residue selected from the group consisting of amino acids at positions 18, 19, 20, 21, 38, 39, 41, 42, 45, 46, 48, 49, 52, 53, 56, 57, 58, 60 and 99 of an HA2 polypeptide.

In an embodiment of the present invention, the epitope of the binding molecule may include amino acid residues at positions 18, 38, 40, 291, 292 and 318 of the HA1 polypeptide. Also, the epitope of the binding molecule may include amino acid residues at positions 18, 19, 20, 21, 41, 42, 45, 48, 49, 52 and 53 of the HA2 polypeptide.

In an embodiment of the present invention, the epitope of the binding molecule may include amino acid residues at positions 18, 38, 40, 291, 292 and 318 of the HA1 polypeptide and may include amino acid residues at positions 18, 19, 20, 21, 41, 42, 45, 48, 49, 52 and 53 of the HA2 polypeptide.

In an embodiment of the present invention, the epitope of the binding molecule may include amino acid residues at positions 278 and 318 of the HA1 polypeptide. Also, the epitope of the binding molecule may include amino acid residues at positions 38, 39, 41, 42, 45, 48, 49, 52, and 53 of the HA2 polypeptide.

In an embodiment of the present invention, the epitope of the binding molecule may include amino acid residues at said positions of the HA1 polypeptide and/or the HA2 polypeptide of a first monomer of HA, and may further include amino acid residues at positions 25, 32 and 33 of the HA1 polypeptide of a second monomer adjacent to the first monomer.

In an embodiment of the present invention, the epitope of the binding molecule may include amino acid residues at positions 278 and 318 of the HA1 polypeptide, and amino acid residues at positions 38, 39, 41, 42, 45, 48, 49, 52, and 53 of the HA2 polypeptide.

In an embodiment of the present invention, the epitope of the binding molecule may include amino acid residues at said positions of the HA1 polypeptide and the HA2 polypeptide of a first monomer of HA, and may further include amino acid residues at positions 25, 32 and 33 of the HA1 polypeptide of a second monomer adjacent to the first monomer.

In an embodiment of the present invention, the epitope of the binding molecule may include amino acid residues at positions 278 and 318 of the HA1 polypeptide, and amino acid residues at positions 38, 39, 41, 42, 45, 48, 49, 52, 53, 58 and 99 of the HA2 polypeptide.

In an embodiment of the present invention, the epitope of the binding molecule may include amino acid residues at said positions of the HA1 polypeptide and the HA2 polypeptide of a first monomer of HA, and may further include amino acid residues at positions 25, 27, 32 and 33 of the HA1 polypeptide of a second monomer adjacent to the first monomer.

In an embodiment of the present invention, the epitope of the binding molecule may include amino acid residues at positions 54, 55, 278, 291 and 318 of the HA1 polypeptide and amino acid residues at positions 19, 20, 21, 38, 39, 41, 42, 45, 46, 48, 49, 52, 53, 56, 57 and 60 of the HA2 polypeptide.

In an embodiment of the present invention, the epitope of the binding molecule may include amino acid residues at said positions of the HA1 polypeptide and the HA2 polypeptide of a first monomer of HA, and may further include amino acid residues at positions 25, 32, 33, 310, 311, and 312 of the HA1 polypeptide of a second monomer of HA adjacent to the first monomer of HA.

The numbering of the amino acid positions of the epitope is based on an H3 HA numbering system.

In an embodiment of the present invention, the binding molecule may include at least one selected from the group consisting of i) a binding molecule, comprising a light-chain variable domain including a CDR1 region of SEQ ID NO:1, a CDR2 region of SEQ ID NO:2 and a CDR3 region of SEQ ID NO:3, and a heavy-chain variable domain including a CDR1 region of SEQ ID NO:4, a CDR2 region of SEQ ID NO:5 and a CDR3 region of SEQ ID NO:6, as determined according to the Kabat method; and ii) a binding molecule, comprising a light-chain variable domain including a CDR1 region of SEQ ID NO:7, a CDR2 region of SEQ ID NO:8 and a CDR3 region of SEQ ID NO:9, and a heavy-chain variable domain including a CDR1 region of SEQ ID NO:10, a CDR2 region of SEQ ID NO:11 and a CDR3 region of SEQ ID NO:12, as determined according to the Kabat method.

In the present invention, CDRs of the variable domains are determined using a typical method in accordance with the system devised by Kabat et al. (Reference [Kabat et al., Sequences of Proteins of Immunological Interest ($5^{th}$), National Institutes of Health, Bethesda, Md. (1991)]). The CDR numbering used in the present invention was performed using the Kabat method, but the present invention also encompasses binding molecules comprising CDRs determined by other methods, including the IMGT method, the Chothia method, and the AbM method, etc.

In an embodiment of the present invention, the binding molecule may include at least one selected from the group consisting of i) a binding molecule including a light chain comprising a polypeptide sequence of SEQ ID NO:13 and a heavy chain comprising a polypeptide sequence of SEQ ID NO:14; and ii) a binding molecule including a light chain comprising a polypeptide sequence of SEQ ID NO:15 and a heavy chain comprising a polypeptide sequence of SEQ ID NO:16.

In an embodiment of the present invention, the binding molecule includes a binding molecule binding to an Fc receptor of a cell surface.

In addition, the present invention provides a vaccine composition comprising the adjuvant composition and a target antigen. The target antigen may be a virus antigen, but is not limited thereto. Preferably, the virus antigen is an influenza virus antigen. The influenza virus antigen includes an influenza A virus or influenza B virus antigen. The influenza virus antigen may be hemagglutinin (HA) or neuraminidase (NA) but is not limited thereto.

Also, in another embodiment of the present invention, the vaccine composition may include the antigen and the adjuvant composition at a weight ratio of 1:0.02 to 1:200, and preferably 1:0.2 to 1:20, but is not limited thereto. The weight ratio of the antigen and the adjuvant composition may be decreased or increased to modulate immunogenic activity.

Also, in another embodiment of the present invention, the present invention provides a vaccine composition added an additional adjuvant composition, in addition to the said adjuvant composition as well as the said adjuvant composition. The additional adjuvant composition may include, but is not limited to, Alum, metabolizable oils (e.g. squalene), tocols (e.g. α-tocopherol), sterols (e.g. cholesterol), saponins (e.g. QS21), Toll-like receptor ligands (e.g. poly (I:C)), an oligonucleotide having a CpG motif and/or LPS derivatives (e.g. 3D-MPL).

In addition, the present invention provides a method of preparing a vaccine composition comprising the adjuvant composition and a target antigen. The vaccine composition may be an influenza virus vaccine composition, but is not limited thereto.

In addition, the present invention provides a method of increasing an immune response to a target antigen by administering the adjuvant composition to a host. The vaccine composition may be an influenza virus vaccine composition, but is not limited thereto.

Also, in another embodiment of the present invention, the immune response may be induced by a cell having an Fc receptor on the surface thereof, but the present invention is not limited thereto.

In addition, the present invention provides a method of preventing a disease caused by virus, comprising administering an effective amount of the vaccine composition containing the adjuvant composition to a subject. For example, the disease caused by a virus may be a disease caused by the influenza virus.

In addition, the present invention provides a method of immunizing a host by administering the vaccine composition to the host.

In addition, the present invention provides a method of preparing an immunological product, comprising a) immunizing a host by administering the vaccine composition to the host and b) obtaining the immunological product from the immunized host.

Also, in another embodiment of the present invention, the immunological product may be T cells, B cells, or an antibody. The immunological product may be other kinds of cells having an Fc receptor on the cell surface, like the B cells, for example, neutrophils, macrophages, natural killer cells or dendritic cells.

Hereinafter, the terms used in the present invention are defined as follows.

As used herein, the term "influenza virus" refers to an enveloped virus belonging to the Orthomyxoviridae family and having a genome composed of eight negative-sense single-stranded RNA (ribonucleic acid) segments. Influenza viruses are classified into groups A, B and C, and are further divided into a number of subtypes depending on HA (hemagglutinin) and NA (neuraminidase) as the major surface proteins thereof 17 types of HA and 10 types of NA have been reported to date.

As used herein, "H1 subtype" includes H1N1, H1N2, H1N3, H1N4, H1N5, H1N6, H1N7, H1N8, H1N9 and H1N10.

As used herein, "H2 subtype" includes H2N1, H2N2, H2N3, H2N4, H2N5, H2N6, H2N7, H2N8, H2N9 and H2N10.

As used herein, "H5 subtype" includes H5N1, H5N2, H5N3, H5N4, H5N5, H5N6, H5N7, H5N8, H5N9 and H5N10.

As used herein, "H9 subtype" includes H9N1, H9N2, H9N3, H9N4, H9N5, H9N6, H9N7, H9N8, H9N9 and H9N10.

As used herein, "1-13 subtype" includes H3N1, H3N2, H3N3, H3N4, H3N5, H3N6, H3N7, H3N8, H3N9 and H3N10.

As used herein, "H7 subtype" includes H7N1, H7N2, H7N3, H7N4, H7N5, H7N6, H7N7, H7N8, H7N9 and H7N10.

As described herein, the term "hemagglutinin" (hereinafter referred to as "HA") refers to the envelope glycoprotein of influenza virus. HA mediates the adsorption and penetration of influenza virus into a host cell. 17 HA subtypes have been reported to date.

As described herein, the term "neuraminidase" (hereinafter referred to as "NA") refers to the envelope glycoprotein of influenza virus. NA plays an important role when influenza viruses have been spread after proliferation. 10 NA subtypes have been reported to date.

As described herein, an influenza vaccine is regarded as being the most effective method of preventing seasonal or pandemic influenza, and largely includes a live vaccine and an inactivated vaccine. As the live vaccine, a live attenuated vaccine is developed and used. The inactivated vaccine may include a whole virus vaccine using the entire virus in which a virus incubated from an embryonated egg or via cell culture is purified and inactivated with formalin or the like, a split vaccine in which the envelope of the virus is disrupted with ether or the like, and a subunit vaccine in which HA and NA components are purified. A vaccine including H1 and H3 subtypes of the influenza A group and one kind from the influenza B group is a trivalent vaccine, and a vaccine including H1 and H3 subtypes of the influenza A group and two kinds from the influenza B group is a tetravalent vaccine.

As described herein, "influenza vaccine" includes all live vaccines and inactivated vaccines, which are trivalent, tetravalent, seasonal, and pandemic.

As described herein, the term "binding molecule" refers to an intact immunoglobulin including monoclonal antibodies, such as chimeric, humanized or human monoclonal antibodies, fusion protein which comprising Fc of immunoglobulin or immunoglobulin which binds to antigen, for example, a variable domain including an immunoglobulin fragment that competes with the intact immunoglobulin in order to bind to the monomeric HA or trimeric HA of influenza A virus, a substrate-binding enzyme, a receptor or a protein. Regardless of the structure, an antigen-binding fragment binds with the same antigen that is recognized by the intact immunoglobulin. The antigen-binding fragment may comprise a peptide or polypeptide comprising an amino acid sequence consisting of at least 2 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of the binding molecule.

As described herein, the term "antigen-binding fragment", particularly, includes Fab, F(ab'), F(ab')2, Fv, dAb, Fd, complementarity-determining region (CDR) fragments, single-chain antibodies (scFv), bivalent single-chain antibodies, single-chain phage antibodies, diabodies, triabodies, tetrabodies, polypeptides that include at least one fragment of an immunoglobulin that is sufficient to confer specific antigen binding to the polypeptide, etc. The above fragments may be produced synthetically or by enzymatic or chemical cleavage of intact immunoglobulins, or they may be genetically engineered by recombinant DNA techniques. Such production methods are well known in the art.

As used herein, the twin "adjuvant" refers to a substance or composition that is added to a vaccine or pharmaceutically active ingredients to thus increase and/or effect an immune response. Examples thereof include an immunogenic carrier or assistant material and/or other pharmaceutically active materials or compositions. Typically, the term "adjuvant" should be interpreted broadly and refers to a broad range of substances or stratagems that may be incorporated into the adjuvant or may enhance the immunogenicity of the antigen administered with the adjuvant. Furthermore, the adjuvant may include, but is not limited to, an immune potentiator, an antigen delivery system or a combination thereof.

As used herein, the term "immunological product" refers to a protective immune mediator or cell generated from the host immunized by the administration of the adjuvant composition and/or the antigen, and examples thereof may include, but are not limited to, activated T cells, B cells or antibodies.

As used herein, the term "pharmaceutically acceptable excipient" means any inert substance that is combined with an active molecule such as a drug, agent, or binding molecule for preparing an admittable or convenient dosage form. The pharmaceutically acceptable excipient is an excipient that is non-toxic or at least less toxic to recipients at the used dosages and concentrations, and is compatible with other ingredients of the formulation comprising the drug, agent or binding molecule.

As used herein, the term "effective amount" refers to an amount of the binding molecule of the invention that is effective for increasing the effect of the vaccine upon administration with the vaccine against influenza A virus.

In the present invention, the already-filed antibodies (Korean Patent Application Nos. 10-2011-0020061, 10-2012-0107512, and 10-2014-0036601) have confirmed their effects of increasing an immune response upon inoculation with the influenza vaccine through mouse experiments, and thus new use thereof as an adjuvant has been found. Here, Korean Patent Application Nos. 10-2011-0020061, 10-2012-0107512, and 10-2014-0036601, filed by the present applicant, are incorporated by reference into this application.

Advantageous Effects

According to the present invention, a composition including at least one binding molecule for neutralizing influenza virus can enhance the effect of a vaccine, and can thus be used as an adjuvant for increasing an immune response upon administration of a vaccine and is very effective at preventing diseases caused by viruses.

FIG. 2 shows the ELISA results of a specific antibody titer against H1N1 HA protein and H1N1 influenza virus in a serum that is sampled 28 days after the first intramuscular injection under the condition that each mouse is intramuscularly injected twice with an H1N1 vaccine composition at an interval of two weeks (Table 3);

FIG. 3 shows changes in the survival rate and body weight of the immunized mouse after inoculating the immunized mouse with $10MLD_{50}$ of H1N1 influenza virus;

FIG. 4 shows the ELISA results of a specific antibody titer against H1N1 influenza virus in a serum that is sampled 13 days, 20 days and 27 days after the first intramuscular injection under the condition that each mouse is intramuscularly injected twice with an H1N1 vaccine composition at an interval of two weeks (Table 5);

FIG. 5 shows changes in the survival rate and body weight of the immunized mouse after inoculating the immunized mouse with $10MLD_{50}$ of H1N1 influenza virus;

FIG. 6 shows the ELISA results of a specific antibody titer against H1N1 influenza virus in a serum that is sampled 13 days, 20 days and 27 days after the first intramuscular injection under the condition that each mouse is intramuscularly injected twice with an H1N1 vaccine composition at an interval of two weeks (Table 7);

FIG. 7 shows changes in the survival rate and body weight of the immunized mouse after inoculating the immunized mouse with $10MLD_{50}$ of H1N1 influenza virus;

FIG. 8 shows the ELISA results of a specific antibody titer against H3N2 influenza virus in a serum that is sampled 13 days and 27 days after the first intramuscular injection under the condition that each mouse is intramuscularly injected twice with an H3N2 vaccine composition at an interval of two weeks (Table 9);

FIG. 9 shows changes in the survival rate and body weight of the immunized mouse after inoculating the immunized mouse with $10MLD_{50}$ of H3N2 influenza virus;

FIG. 10 shows the ELISA results of a specific antibody titer against H1N1 influenza virus in a serum is sampled 13 days, 20 days and 27 days after the first intramuscular injection under the condition that each mouse is intramuscularly injected twice with an H1N1 vaccine composition at an interval of two weeks (Table 11);

FIG. 11 shows the results of measurement the proportion of the B cell population among immune cells in the spleen 1 day, 3 days and 7 days after the second intramuscular injection under the condition that each mouse is intramuscularly injected twice with an H1N1 vaccine composition at an interval of two weeks (Table 14);

FIG. 12 shows the results of measurement the proportion of the B cell population among immune cells in the inguinal lymph node 1 day, 3 days and 7 days after the second intramuscular injection under the condition that each mouse is intramuscularly injected twice with an H1N1 vaccine composition at an interval of two weeks (Table 14);

FIG. 13 shows the results of measurement the proportion of the B cell population in the spleen and lymph nodes 1 day and 3 days after inoculation with H1N1 virus 4 weeks after the second intramuscular injection under the condition that each mouse is intramuscularly injected twice with an H1N1 vaccine composition at an interval of two weeks (Table 15); and FIG. 14 shows the ELISA results of a specific antibody titer against H1N1 influenza virus in a serum that is sampled 13 days, 20 days and 27 days after the first intramuscular injection under the condition that each mouse is intramuscularly injected twice with an H1N1 vaccine composition at an interval of two weeks (Table 16).

MODE FOR INVENTION

Hereinafter, the present invention will be explained in more detail with reference to the following examples. However, the following examples and test examples are provided only to illustrate the present invention but are not to be construed as the limit of present invention. The documents cited in the present invention are incorporated by reference into description of the present invention.

EXAMPLES

Example 1

Evaluation of Vaccine Adjuvant Effect of Influenza Virus-Neutralizing Antibody 1-1. ELISA In order to evaluate the effect of therapeutic CT120 and CT149 antibodies as an influenza virus vaccine adjuvant, as set forth in Table 1 below, animal testing was performed. As shown in Table 1 below, 0.2 μg of H1N1 split vaccine was administered alone, or in combination with an adjuvant Alum (1 mg) typically used as an adjuvant or a CT120 antibody (0.5 μg, 1 μg, 5 μg, 10 μg) or a CT149 antibody (0.5 μg, 1 μg, 5 μg, 10 μg) as an adjuvant, after which the antibody titer against influenza virus in each mouse was measured.

TABLE 1

| Group | Antigen | Adjuvant | Route | Mouse # |
|---|---|---|---|---|
| Group 1 | PBS | — | i.m. | 4 |
| Group 2 | PBS | CT 120 10 μg | i.m. | 4 |
| Group 3 | PBS | CT 149 10 μg | i.m. | 4 |
| Group 4 | H1N1 split vaccine 0.2 μg | — | i.m. | 4 |
| Group 5 | H1N1 split vaccine 0.2 μg | CT 120 10 μg | i.m. | 4 |
| Group 6 | H1N1 split vaccine 0.2 μg | CT 120 5 μg | i.m. | 4 |
| Group 7 | H1N1 split vaccine 0.2 μg | CT120 1 μg | i.m. | 4 |
| Group 8 | H1N1 split vaccine 0.2 μg | CT120 0.5 μg | i.m. | 4 |
| Group 9 | H1N1 split vaccine 0.2 μg | CT149 10 μg | i.m. | 4 |
| Group 10 | H1N1 split vaccine 0.2 μg | CT149 5 μg | i.m. | 4 |
| Group 11 | H1N1 split vaccine 0.2 μg | CT149 1 μg | i.m. | 4 |
| Group 12 | H1N1 split vaccine 0.2 μg | CT149 0.5 μg | i.m. | 4 |
| Group 13 | H1N1 split vaccine 0.2 μg | Alum | i.m. | 4 |

As set forth in Table 1, the H1N1 vaccine composition was intramuscularly injected twice to mice at an interval of two weeks, after which the immune response induced in each test group was observed. 13 days, 17 days and 27 days after the first intramuscular injection, the serum was sampled from each test group and the antibody titer thereof was measured through ELISA.

As seen in the results of FIG. 1, the antibody able to detect a virus corresponding to the vaccine administered as a whole was produced in a larger amount in the groups administered with the vaccine in combination with CT120, CT149 or Alum than in the group administered only with the vaccine. When comparing the amounts of the antibodies 27 days after administration of the vaccine and the adjuvant, the amounts of the produced antibodies were similar in the group administered with 5 μg of CT120 or 10 μg of CT149 and the group administered with Alum, and the group administered with 1 μg or 0.5 μg of CT149 produced the antibody in a large amount compared to the group administered with Alum.

1-2. Hemagglutinin Inhibition Assay (HI Assay)

As shown in Table 2 below, in order to verify whether the therapeutic antibodies CT120 and CT149 are effective as an influenza virus vaccine adjuvant, the effectiveness of the vaccine was evaluated through hemagglutinin inhibition assay (HI assay). 13 days, 17 days and 27 days after administration of the vaccine and the adjuvant, the serum was obtained from each mouse, and the antibody titer able to inhibit the hemagglutination of influenza virus and chicken erythrocyte was measured.

TABLE 2

| | | | HI titer | | |
|---|---|---|---|---|---|
| Group | Antigen | Adjuvant | Day 13 | Day 17 | Day 27 |
| Group 1 | PBS | — | N.D. | N.D. | N.D. |
| Group 2 | PBS | CT 120 10 μg | N.D. | N.D. | N.D. |
| Group 3 | PBS | CT 149 10 μg | N.D. | N.D. | N.D. |
| Group 4 | H1N1 split vaccine 0.2 μg | — | N.D. | N.D. | 40 |
| Group 5 | H1N1 split vaccine 0.2 μg | CT 120 10 μg | N.D. | N.D. | 40 |
| Group 6 | H1N1 split vaccine 0.2 μg | CT 120 5 μg | N.D. | N.D. | 80 |
| Group 7 | H1N1 split vaccine 0.2 μg | CT120 1 μg | N.D. | N.D. | 40 |
| Group 8 | H1N1 split vaccine 0.2 μg | CT120 0.5 μg | N.D. | N.D. | 40 |
| Group 9 | H1N1 split vaccine 0.2 μg | CT149 10 μg | N.D. | N.D. | 80 |
| Group 10 | H1N1 split vaccine 0.2 μg | CT149 5 μg | N.D. | N.D. | 40 |
| Group 11 | H1N1 split vaccine 0.2 μg | CT149 1 μg | N.D. | 40 | 160 |
| Group 12 | H1N1 split vaccine 0.2 μg | CT149 0.5 μg | N.D. | N.D. | 160 |
| Group 13 | H1N1 split vaccine 0.2 μg | Alum | N.D. | 20 | 80 |

As in the results of FIG. 1, when comparing the amounts of the antibodies 27 days after administration of the vaccine and the adjuvant, the groups administered with 5 μg of CT120 and 10 μg of CT149 (Groups 6 and 9) exhibited an HI titer similar to that of the group administered with Alum (Group 13), and the groups administered with 1 μg and 0.5 μg of CT149 (Groups 11 and 12) exhibited high HI titer compared to the group administered with Alum.

When CT120 or CT149 was administered together upon injection of the influenza virus vaccine, an immunogenicity-enhancing effect similar or superior to that of the Alum adjuvant was manifested. Thereby, CT120 and CT149 can be found to be effective as the influenza virus vaccine adjuvant.

Example 2

Determination of Antigen Concentration to Verify the Adjuvant Effect of CT120 and CT149 Using H1N1 Vaccine as Antigen 2-1. Antibody Production Result As shown in Table 3 below, animal testing was performed to determine the appropriate antigen concentration before the verification of the adjuvant effect of the therapeutic antibody. H1N1 vaccine (cell-based) in an amount ranging from 0.01 µg to 1 µg was administered alone or in combination with an Alum adjuvant, after which the antibody titers were measured through ELISA, and the neutralizing antibody titers were measured through HI. "Standard" indicates a commercially available trivalent vaccine, and was used for comparison of test results.

TABLE 3

| Group | Ag | Adjuvant | Route | Mouse # |
|---|---|---|---|---|
| Group 1 | PBS | — | i.m. | 5 |
| Group 2 | H1N1 vaccine 1 µg | — | i.m. | 5 |
| Group 3 | H1N1 vaccine 1 µg | Alum | i.m. | 5 |
| Group 4 | Standard 3 µg | — | i.m. | 5 |
| Group 5 | H1N1 vaccine 0.5 µg | — | i.m. | 5 |
| Group 6 | H1N1 vaccine 0.5 µg | Alum | i.m. | 5 |
| Group 7 | H1N1 vaccine 0.2 µg | — | i.m. | 5 |
| Group 8 | H1N1 vaccine 0.2 µg | Alum | i.m. | 5 |
| Group 9 | H1N1 vaccine 0.1 µg | — | i.m. | 5 |
| Group 10 | H1N1 vaccine 0.1 µg | Alum | i.m. | 5 |
| Group 11 | Standard 0.3 µg | — | i.m. | 5 |
| Group 12 | H1N1 vaccine 0.05 µg | — | i.m. | 5 |
| Group 13 | H1N1 vaccine 0.05 µg | Alum | i.m. | 5 |
| Group 14 | H1N1 vaccine 0.01 µg | — | i.m. | 5 |
| Group 15 | H1N1 vaccine 0.01 µg | Alum | i.m. | 5 |
| Group 16 | Standard 0.03 µg | — | i.m. | 5 |

As set forth in Table 3, the H1N1 vaccine composition was intramuscularly injected twice to mice at an interval of two weeks, after which the immune response induced in each test group was observed. 28 days after the first intramuscular injection, the serum was sampled from each test group and the antibody titer against HA protein and virus in the serum was measured through ELISA and the neutralizing antibody titer was measured through HI assay.

Figure 1:
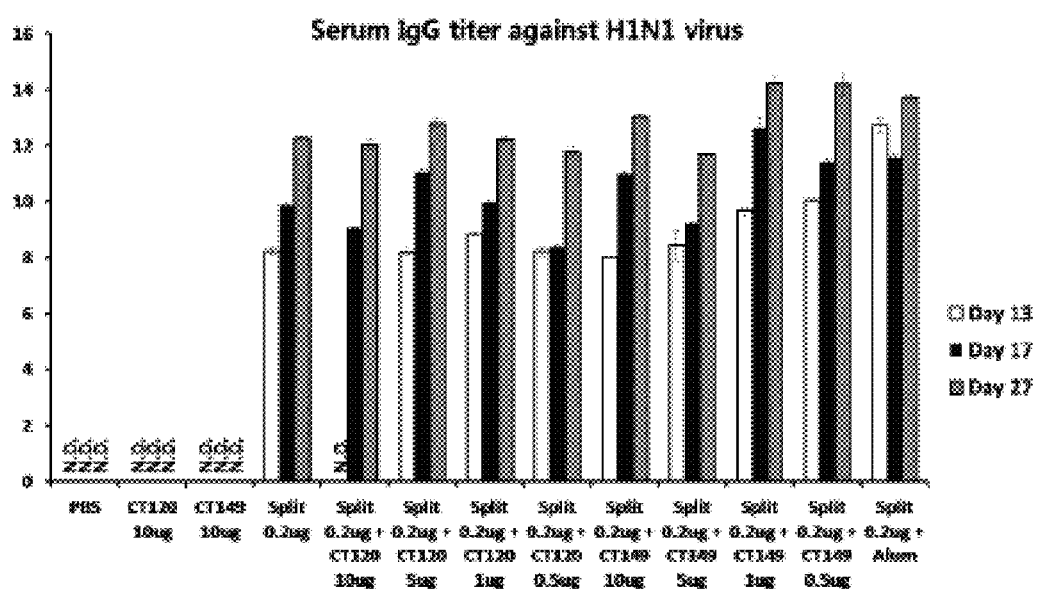
FIG. 1 shows the ELISA results of a specific antibody titer against H1N1 influenza virus in a serum that is sampled 13 days, 17 days and 27 days after the first intramuscular injection under the condition that each mouse is intramuscularly injected twice with an H1N1 vaccine composition at an interval of two weeks (Table 1);
Figure 2:
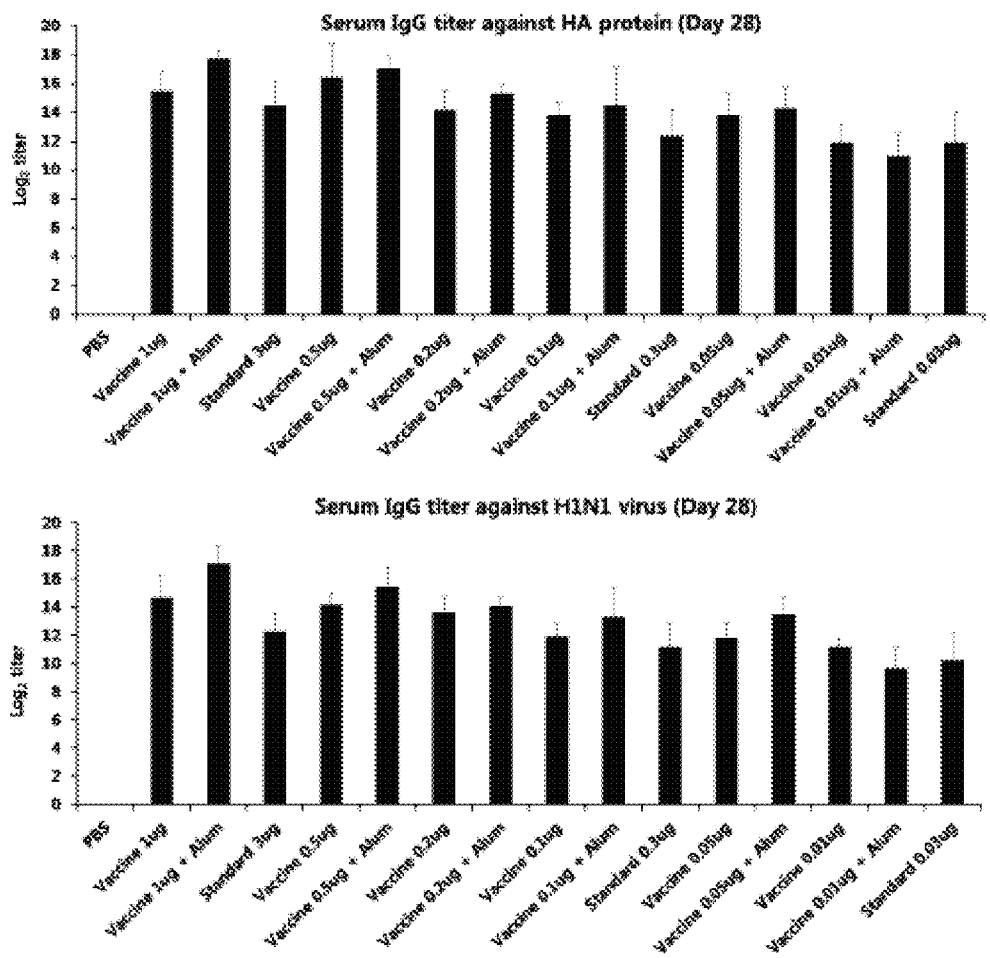

As seen in the results of FIG. 2, the antibody titer was increased in approximate proportion to the amount of the antigen that was added, and the antibody titer was higher when the Alum adjuvant was added therewith. Furthermore, there was no great difference between the antibody titer against HA protein and the antibody titer against H1N1 virus.

TABLE 4

| Group | | HI titer |
|---|---|---|
| Group 1 | PBS | N.D. |
| Group 2 | H1N1 1 µg | 160 |
| Group 3 | H1N1 1 µg + alum | 1280 |
| Group 4 | Standard 3 µg | 80 |
| Group 5 | H1N1 0.5 µg | 160 |
| Group 6 | H1N1 0.5 µg + alum | 320 |
| Group 7 | H1N1 0.2 µg | 80 |
| Group 8 | H1N1 0.2 µg + alum | 160 |
| Group 9 | H1N1 0.1 µg | 20 |
| Group 10 | H1N1 0.1 µg + alum | 160 |
| Group 11 | Standard 0.3 µg | N.D. |
| Group 12 | H1N1 0.05 µg | 20 |
| Group 13 | H1N1 0.05 µg + alum | 80 |

TABLE 4-continued

| Group | | HI titer |
|---|---|---|
| Group 14 | H1N1 0.01 µg | N.D. |
| Group 15 | H1N1 0.01 µg + alum | N.D. |
| Group 16 | Standard 0.03 µg | N.D. |

As is apparent from the results of Table 4, the HI titer was increased in the test groups administered with the antigen and Alum compared to the test groups administered only with the antigen. Furthermore, in the test groups having an antigen concentration of 0.1 µg (Groups 9 and 10) and the test groups having an antigen concentration of 0.05 µg (Groups 12 and 13), the HI titer was increased 8 times and 4 times respectively when the Alum adjuvant was further added compared to when only the antigen was added, whereby a difference in the vaccine effects with or without the adjuvant was clearly confirmed.

2-2. Protective Immunity Result

In order to evaluate the protective immunity against influenza virus, 4 weeks after the second immunization, 10MLD$_{50}$ of CA/04/09 H1N1 virus was inoculated to the immunized mouse nasal cavity and allowed to infect it, after which changes in the survival rate and body weight of each mouse were measured for 15 days.

Figure 3:
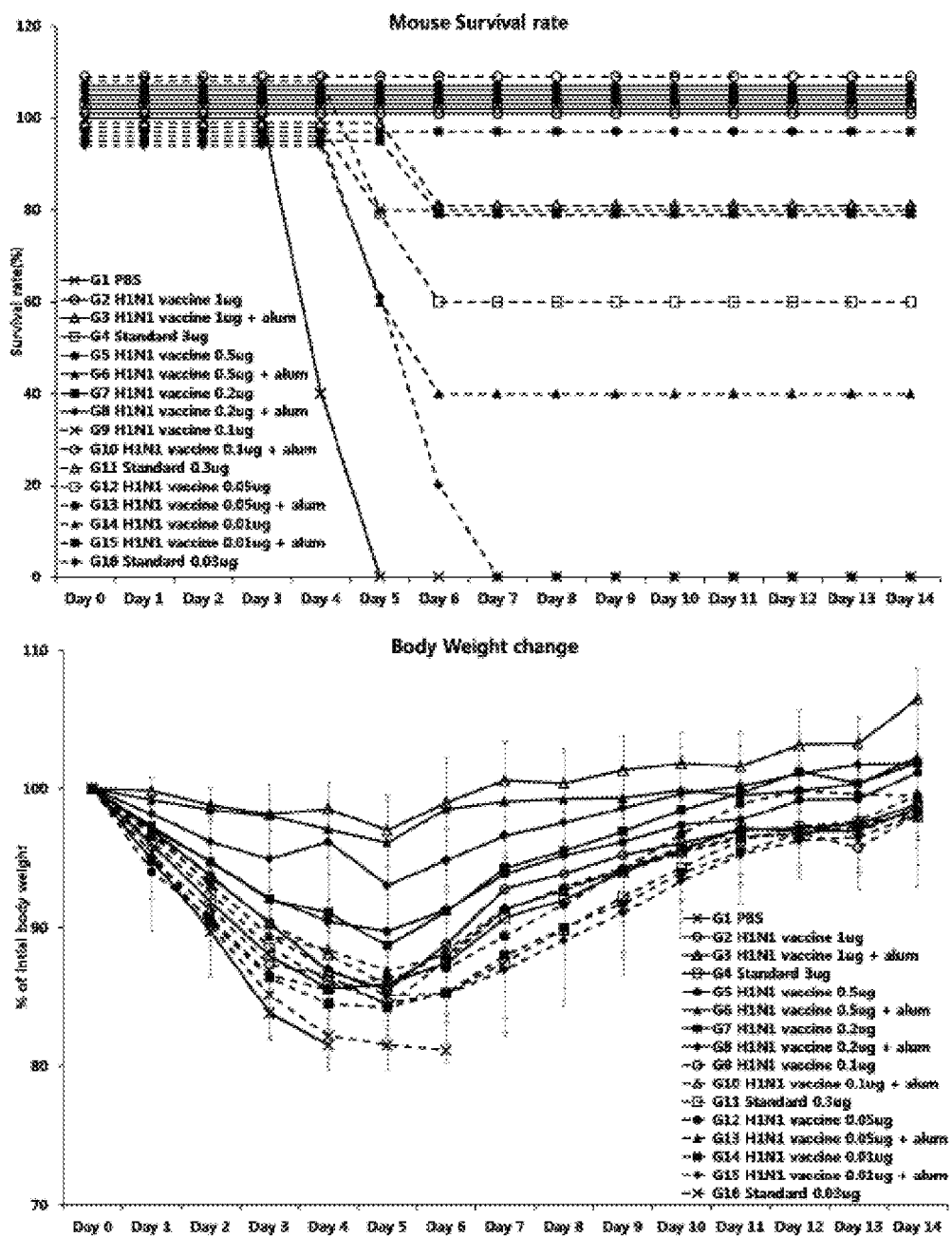

As shown in the results of FIG. 3, the protective immunity effect against influenza virus was high at all concentrations in the test groups administered with the antigen and the adjuvant compared to the test group administered only with the antigen. Furthermore, as for the test groups of two antigen concentrations (0.1 µg and 0.05 µg) at which the vaccine effect was significantly different in the presence or absence of the adjuvant through HI titer measurement, in the 0.1 µg test groups, the test group administered only with the antigen exhibited a survival rate of 80% and the test group administered with the antigen and the adjuvant showed a survival rate of 100%. On the other hand, in the 0.05 µg test groups, the test group administered only with the antigen exhibited a survival rate of 60% and the test group administered with the antigen and the adjuvant showed a survival rate of 100%.

2-3. Conclusion

Based on the HI titer results and the protective immunity effects against influenza virus, as for the 0.1 µg test groups, the HI titer results were different but a difference in the protective immunity effects depending on whether or not the adjuvant was present was low, and thus, 0.05 µg, at which differences in the HI titer results and the protective immunity effects were significant depending on whether or not the adjuvant was present, was determined as the ultimate antigen concentration. Subsequently, animal testing was performed to evaluate the adjuvant effect using the same.

Example 3

Evaluation of Adjuvant Effect of CT120 and CT149 Using H1N1 Vaccine as Antigen 3-1. Evaluation of Adjuvant Effect of CT120 using H1N1 Vaccine as Antigen 3-1-1. Antibody Production Result Using an antigen concentration of 0.05 µg, determined based on the animal test results (Example 2), animal testing for verifying the adjuvant effects of therapeutic antibodies CT120 and CT149 was carried out. Here, in mouse testing, the adjuvant effects of CT120 (mIgG2a) and CT149

(mIgG2a), corresponding to the mouse forms of CT120 and CT149 antibodies, are expected to be effective compared to CT120 or CT149, and thus all of CT120 and CT149 and mouse forms thereof were used for animal testing.

The mouse-form antibody was manufactured by replacing the constant region of the Fc region in CT120 or CT149, which is the human IgG1 form, with the IgG1 or IgG2a region of the mouse.

The amounts of CT120 and CT120 (mIgG2a) were determined by selecting the concentrations effective as the adjuvant through the preliminary test (not described herein).

The H1N1 vaccine (cell-based) was mixed with the therapeutic antibody at various concentrations, reacted at 37° C. for 1 hr, and intramuscularly injected twice to mice at an interval of 2 weeks, as shown in Table 5 below. 13 days, 20 days, and 27 days after the first intramuscular injection, the serum was sampled in each test group and the antibody titer against H1N1 virus in the serum and the neutralizing antibody titer were measured through ELISA and HI assay, respectively.

TABLE 5

| Group | Ag | Adjuvant | Route | Mouse # |
|---|---|---|---|---|
| Group 1 | PBS | — | i.m. | 10 |
| Group 2 | PBS | CT 120 0.5 µg | i.m. | 10 |
| Group 3 | PBS | CT 120 (mIgG2a) 0.5 µg | i.m. | 10 |
| Group 4 | H1N1 vaccine 0.05 µg | — | i.m. | 10 |
| Group 5 | H1N1 vaccine 0.05 µg | CT 120 0.05 µg | i.m. | 10 |
| Group 6 | H1N1 vaccine 0.05 µg | CT 120 0.1 µg | i.m. | 10 |
| Group 7 | H1N1 vaccine 0.05 µg | CT 120 0.5 µg | i.m. | 10 |
| Group 8 | H1N1 vaccine 0.05 µg | CT 120 (mIgG2a) 0.05 µg | i.m. | 10 |
| Group 9 | H1N1 vaccine 0.05 µg | CT 120 (mIgG2a) 0.1 µg | i.m. | 10 |
| Group 10 | H1N1 vaccine 0.05 µg | CT 120 (mIgG2a) 0.5 µg | i.m. | 10 |
| Group 11 | H1N1 vaccine 0.05 µg | Alum | i.m. | 10 |
| Group 12 | Standard 0.15 µg | — | i.m. | 10 |

Figure 4:
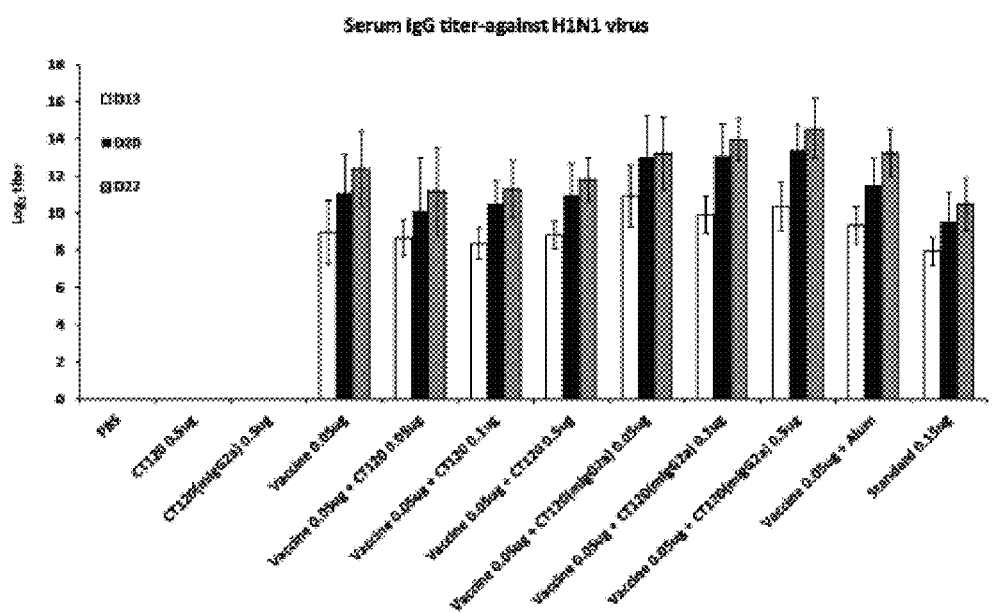

As seen in the results of FIG. 4, the antibody titer against H1N1 virus was higher in the test group using the mouse-form CT120 (mIgG2a) as the adjuvant than in the test group using CT120 as the adjuvant. Furthermore, in the case of the test group using CT120 (mIgG2a), the antibody titer was high compared to the test group using Alum as the adjuvant, and the antibody titer was drastically increased in the serum (D20 of FIG. 5) sampled 3 weeks after the first immunization.

TABLE 6

| | Ag | Adjuvant | HI titer |
|---|---|---|---|
| G1 | PBS | — | N.D. |
| G2 | PBS | CT 120 0.5 µg | N.D. |
| G3 | PBS | CT 120 (mIgG2a) 0.5 µg | N.D. |
| G4 | H1N1 vaccine 0.05 µg | — | 20 |
| G5 | H1N1 vaccine 0.05 µg | CT 120 0.05 µg | 40 |
| G6 | H1N1 vaccine 0.05 µg | CT 120 0.1 µg | 20 |
| G7 | H1N1 vaccine 0.05 µg | CT 120 0.5 µg | 20 |
| G8 | H1N1 vaccine 0.05 µg | CT 120 (mIgG2a) 0.05 µg | 40 |
| G9 | H1N1 vaccine 0.05 µg | CT 120 (mIgG2a) 0.1 µg | 80 |
| G10 | H1N1 vaccine 0.05 µg | CT 120 (mIgG2a) 0.5 µg | 160 |
| G11 | H1N1 vaccine 0.05 µg | Alum | 80 |
| G12 | Standard 0.15 µg | — | N.D. |

As is apparent from the results of Table 6, the HI titer was generally increased a maximum of 4 times depending on the concentration in the test group using CT120 (mIgG2a) as the adjuvant compared to the test group using CT120 as the adjuvant. The test group (Group 10) using 0.5 µg of CT120 (mIgG2a), having the highest antibody titer, exhibited the highest HI titer, specifically 160, among all test groups.

3-1-2. Protective Immunity Result

In order to evaluate the protective immunity against influenza virus, 4 weeks after the second immunization, 10MLD$_{50}$ of CA/04/09 H1N1 virus was inoculated to the immunized mouse nasal cavity and allowed to infect it, after which changes in the survival rate and body weight of each mouse were measured for 15 days.

Figure 5:
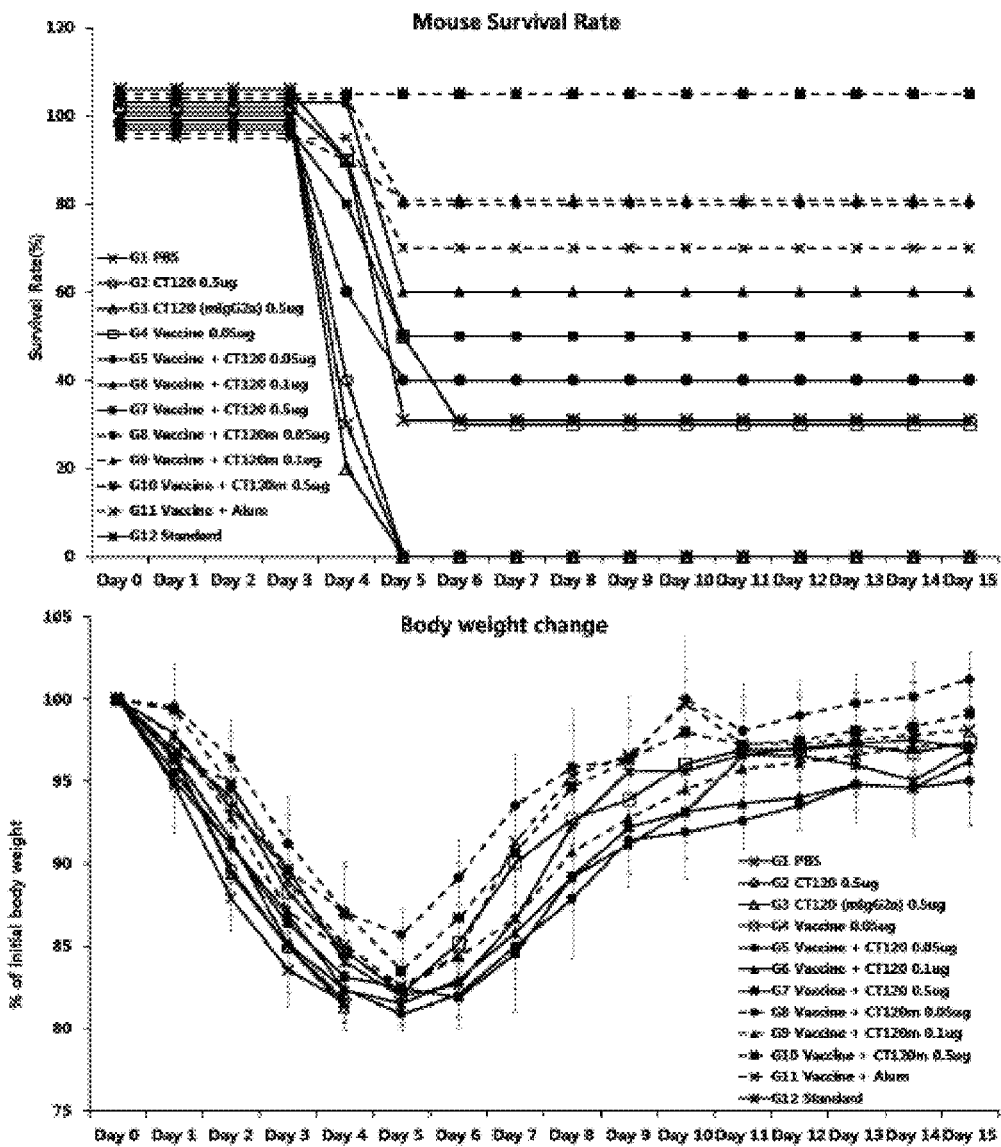

As seen in the results of FIG. 5, when CT120 (mIgG2a) was used as the adjuvant, the survival rate was higher than in the test group using CT120 as the adjuvant or the test group using only the antigen, and the changes in body weight were the lowest. In particular, the test group using, as the adjuvant, 0.5 µg of CT120 (mIgG2a), having the highest antibody titer and HI titer results, exhibited a survival rate of 100%, which is 30% higher than that of the test group using Alum as the adjuvant.

Thereby, CT120 (mIgG2a) can be found to be more effective as the adjuvant compared to CT120 and to manifest the greatest effect when administered at a concentration of 0.5 µg.

3-2. Evaluation of Adjuvant Effect of CT149 Using H1N1 Vaccine as Antigen 3-2-1. Antibody Production Result As shown in Table 7 below, the concentration at which the adjuvant effect was exhibited in the preliminary test (not described herein) for CT149 was determined, and the same testing as in Example 3-1-1 was carried out.

TABLE 7

| Group | Ag | Adjuvant | Route | Mouse # |
|---|---|---|---|---|
| Group 1 | PBS | — | i.m. | 10 |
| Group 2 | PBS | CT 149 0.5 µg | i.m. | 10 |
| Group 3 | PBS | CT 149 (mIgG2a) 0.5 µg | i.m. | 10 |
| Group 4 | H1N1 vaccine 0.05 µg | — | i.m. | 10 |
| Group 5 | H1N1 vaccine 0.05 µg | CT 149 0.01 µg | i.m. | 10 |
| Group 6 | H1N1 vaccine 0.05 µg | CT 149 0.05 µg | i.m. | 10 |
| Group 7 | H1N1 vaccine 0.05 µg | CT 149 0.5 µg | i.m. | 10 |
| Group 8 | H1N1 vaccine 0.05 µg | CT 149 (mIgG2a) 0.01 µg | i.m. | 10 |
| Group 9 | H1N1 vaccine 0.05 µg | CT 149 (mIgG2a) 0.05 µg | i.m. | 10 |
| Group 10 | H1N1 vaccine 0.05 µg | CT 149 (mIgG2a) 0.5 µg | i.m. | 10 |
| Group 11 | H1N1 vaccine 0.05 µg | Alum | i.m. | 10 |
| Group 12 | Standard 0.15 µg | — | i.m. | 10 |

Figure 6:
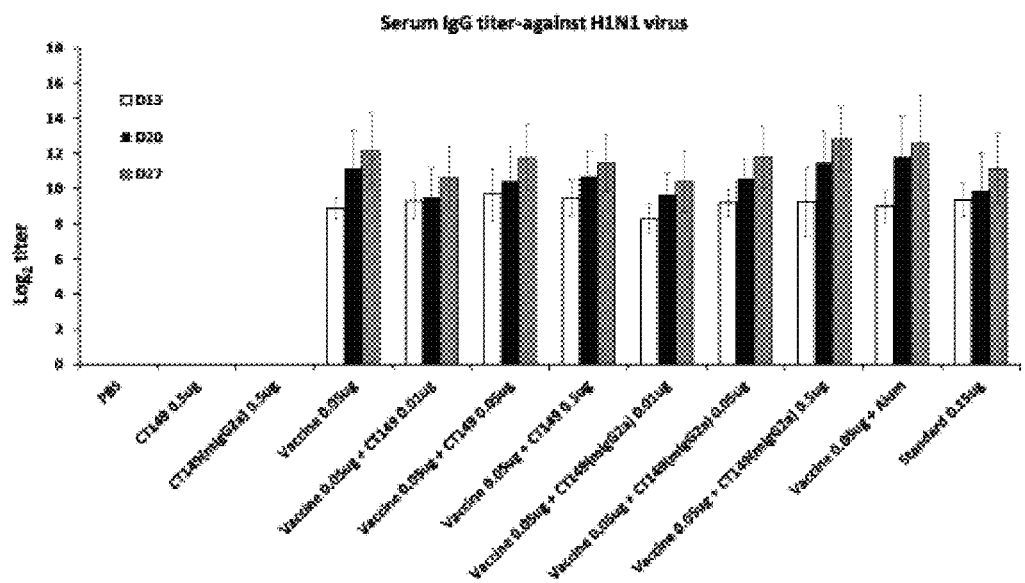

As seen in the results of FIG. 6, the adjuvant effect of CT149 was generally weak, unlike CT120, and the antibody titer similar to the test group using the Alum adjuvant was represented in the test group using 0.5 µg of CT149 (mIgG2a).

TABLE 8

| | Ag | Adjuvant | HI titer |
|---|---|---|---|
| G1 | PBS | — | N.D. |
| G2 | PBS | CT 149 0.5 µg | N.D. |
| G3 | PBS | CT 149 (mIgG2a) 0.5 µg | N.D. |
| G4 | H1N1 vaccine 0.05 µg | — | 20 |
| G5 | H1N1 vaccine 0.05 µg | CT 149 0.01 µg | 20 |
| G6 | H1N1 vaccine 0.05 µg | CT 149 0.05 µg | 40 |
| G7 | H1N1 vaccine 0.05 µg | CT 149 0.5 µg | 20 |
| G8 | H1N1 vaccine 0.05 µg | CT 149 (mIgG2a) 0.01 µg | 20 |
| G9 | H1N1 vaccine 0.05 µg | CT 149 (mIgG2a) 0.05 µg | 40 |
| G10 | H1N1 vaccine 0.05 µg | CT 149 (mIgG2a) 0.5 µg | 80 |

TABLE 8-continued

| Ag | Adjuvant | HI titer |
|---|---|---|
| G11 | H1N1 vaccine 0.05 µg | Alum | 80 |
| G12 | Standard 0.15 µg | — | N.D. |

As is apparent from the results of Table 8, the HI titer was not significantly increased in the test group using CT149 or CT149 (mIgG2a) as the adjuvant, and as in the results of antibody titer measured through ELISA, the HI titer in the test group using 0.5 µg of CT149 (mIgG2a) (Group 10) was the same as that in the test group using the Alum adjuvant (Group 11).

3-2-2. Protective Immunity Result

In order to evaluate the protective immunity against influenza virus, 4 weeks after the second immunization, 10MLD$_{50}$ of CA/04/09 H1N1 virus was inoculated to the immunized mouse nasal cavity and allowed to infect it, after which changes in the survival rate and body weight of each mouse were measured for 15 days.

Figure 7:
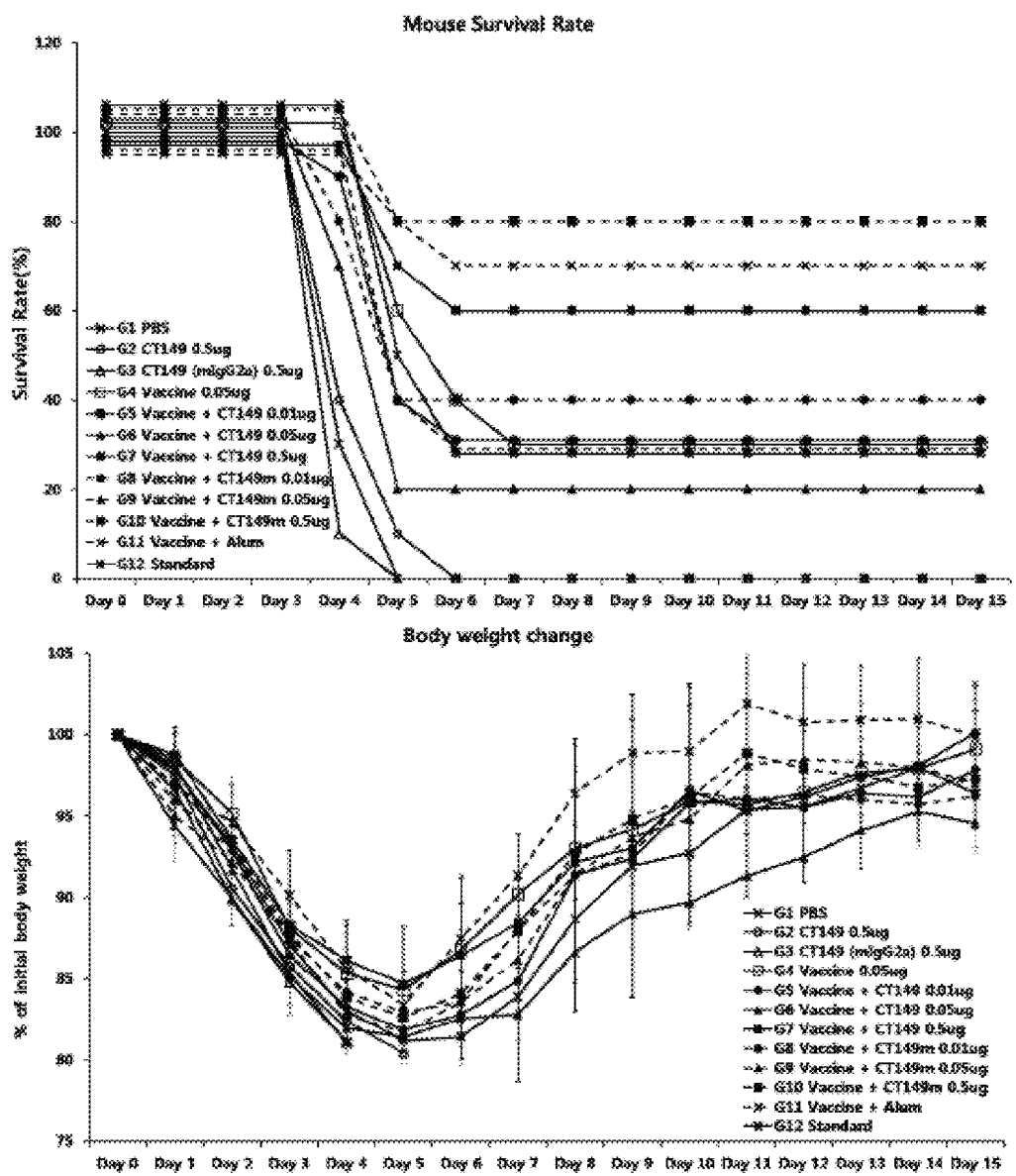

As seen in the results of FIG. 7, the test group using 0.5 µg of CT149 (mIgG2a) as the adjuvant exhibited a survival rate of 80%, which is 10% higher than when using Alum. The extent of changing the body weight was not significantly improved compared to when using Alum.

3-3. Conclusion

Based on the above results, CT120 (mIgG2a) exhibited an outstanding adjuvant effect for the H1N1 vaccine, especially the greatest effect when used at a concentration of 0.5 µg. When CT149 (mIgG2a) was used at 0.5 µg, the adjuvant effect was exhibited, but was lower than that of CT120 (mIgG2a).

Example 4

Evaluation of Adjuvant Effect of CT120 and CT149 Using H3N2 Vaccine as Antigen

The effects of CT120 and CT149 as the adjuvant for H1N1 vaccine were confirmed through Examples 1 to 3, and, using another influenza virus strain, Philippines/2/82 (H3N2), H3N2 vaccine (cell-based) was produced, and animal testing was performed to evaluate the effects of CT120 and CT149 as the adjuvant for H3N2 vaccine.

4-1. Antibody Production Result

As shown in Table 9 below, animal testing was performed to determine the appropriate antigen concentration before verification of the adjuvant effect of the therapeutic antibody. H3N2 vaccine in an amount ranging from 0.01 µg to 1 µg was administered alone or in combination with the Alum adjuvant, after which the antibody titers were measured through ELISA and the neutralizing antibody titers were measured through HI. Furthermore, in order to evaluate the protective immunity effect, each mouse was infected with mouse-adapted Philippines/2/82(H3N2) virus and changes in the survival rate and body weight thereof were measured.

TABLE 9

| Group | Ag | Adjuvant | Route | Mouse # |
|---|---|---|---|---|
| Group 1 | PBS | — | i.m. | 5 |
| Group 2 | H3N2 vaccine 1 µg | — | i.m. | 5 |
| Group 3 | H3N2 vaccine 1 µg | Alum | i.m. | 5 |
| Group 4 | H3N2 vaccine 0.5 µg | — | i.m. | 5 |
| Group 5 | H3N2 vaccine 0.5 µg | Alum | i.m. | 5 |
| Group 6 | H3N2 vaccine 0.2 µg | — | i.m. | 5 |
| Group 7 | H3N2 vaccine 0.2 µg | Alum | i.m. | 5 |
| Group 8 | H3N2 vaccine 0.1 µg | — | i.m. | 5 |
| Group 9 | H3N2 vaccine 0.1 µg | Alum | i.m. | 5 |
| Group 10 | H3N2 vaccine 0.05 µg | — | i.m. | 5 |
| Group 11 | H3N2 vaccine 0.05 µg | Alum | i.m. | 5 |
| Group 12 | H3N2 vaccine 0.01 µg | — | i.m. | 5 |
| Group 13 | H3N2 vaccine 0.01 µg | Alum | i.m. | 5 |

As set forth in Table 9, the H3N2 vaccine composition was intramuscularly injected twice to mice at an interval of two weeks, after which the immune response induced in each test group was observed. 2 weeks after each intramuscular injection, the serum was sampled from each test group and the antibody titer against H3N2 virus in the serum was measured through ELISA and the neutralizing antibody titer was measured through HI assay.

Figure 8:
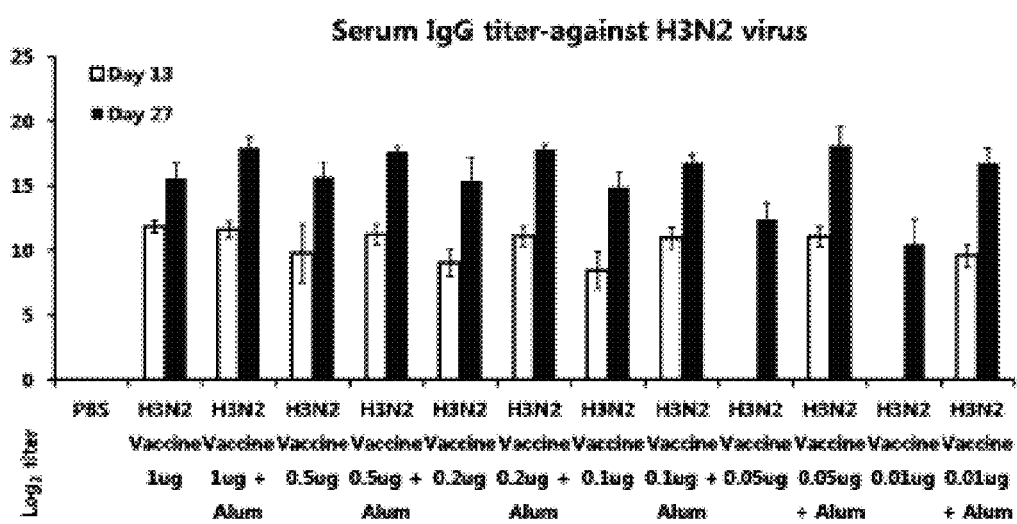

As seen in the results of FIG. 8, the antibody titer was increased in proportion to the amount of the antigen that was added, and the antibody titer was higher when used together with the Alum adjuvant.

TABLE 10

| Group | Ag | Adjuvant | HI titer |
|---|---|---|---|
| Group 1 | PBS | — | N.D. |
| Group 2 | H3N2 vaccine 1 µg | — | 160 |
| Group 3 | H3N2 vaccine 1 µg | Alum | 320 |
| Group 4 | H3N2 vaccine 0.5 µg | — | 160 |
| Group 5 | H3N2 vaccine 0.5 µg | Alum | 320 |
| Group 6 | H3N2 vaccine 0.2 µg | — | 80 |
| Group 7 | H3N2 vaccine 0.2 µg | Alum | 640 |
| Group 8 | H3N2 vaccine 0.1 µg | — | 80 |
| Group 9 | H3N2 vaccine 0.1 µg | Alum | 320 |
| Group 10 | H3N2 vaccine 0.05 µg | — | N.D. |
| Group 11 | H3N2 vaccine 0.05 µg | Alum | 640 |
| Group 12 | H3N2 vaccine 0.01 µg | — | N.D. |
| Group 13 | H3N2 vaccine 0.01 µg | Alum | 160 |

As is apparent from the results of Table 10, the HI titer was higher in the test group using the antigen and Alum than in the test group using only the antigen. In the test groups using 0.01 µg and 0.05 µg of the antigen (Groups 12 and 10), the HI titer could not be measured, but the HI titers were increased to 160 and 640 in the test groups further added with the Alum as adjuvant (Groups 13 and 11), respectively.

4-2. Protective Immunity Result

In order to evaluate the protective immunity against influenza virus, 4 weeks after the second immunization, 10MLD$_{50}$ of A/Philippines/2/82 H3N2 virus was inoculated to the immunized mouse nasal cavity and allowed to infect it, after which changes in the survival rate and body weight of each mouse were measured for 15 days.

Figure 9:
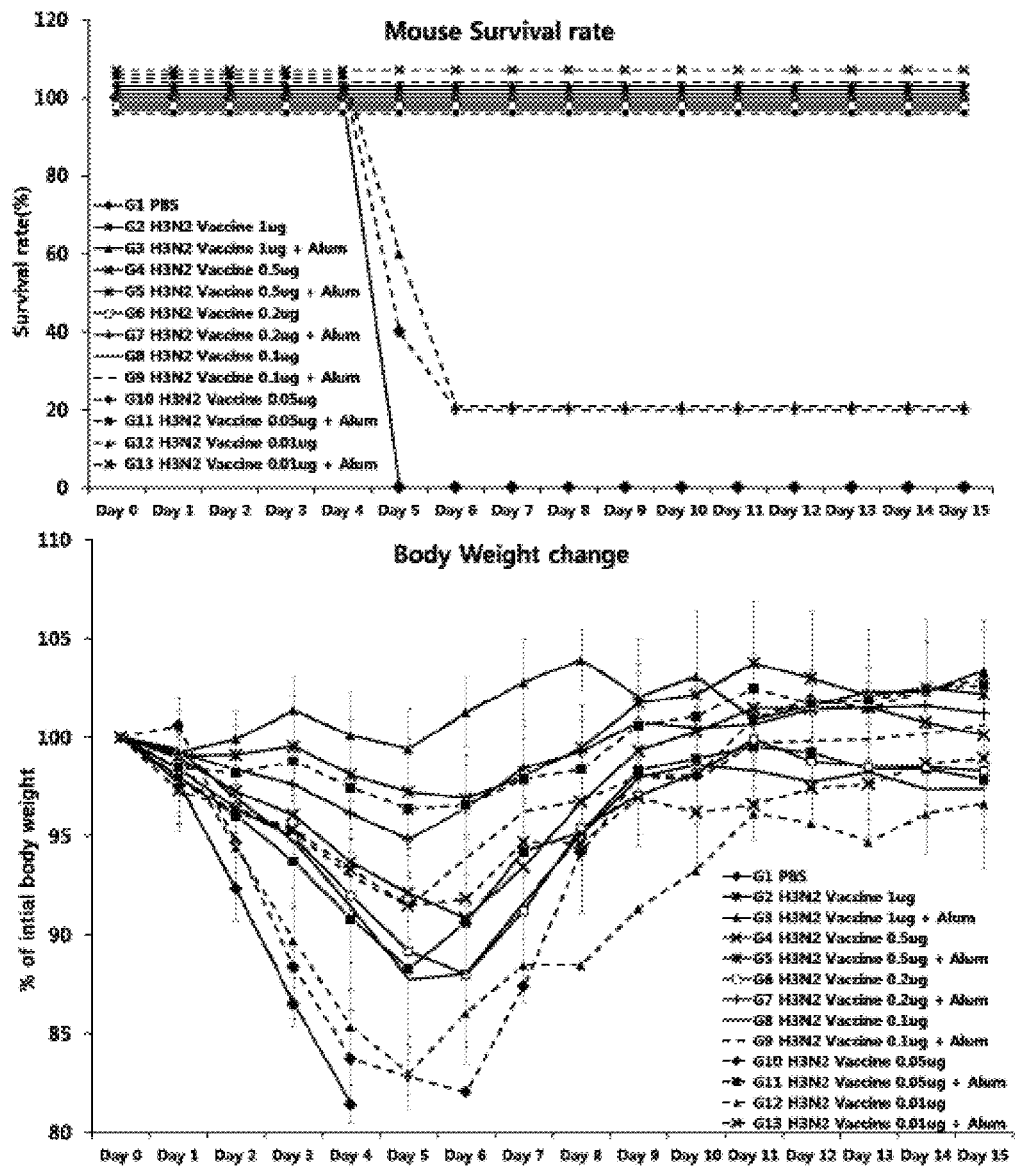
Figure 10:
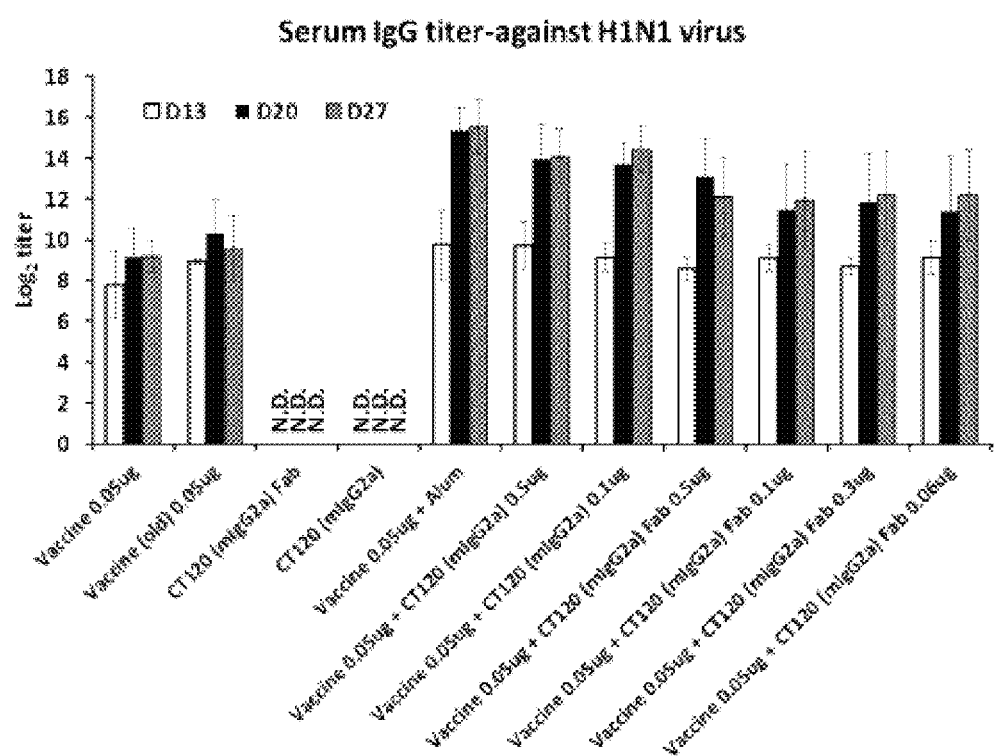

As shown in the results of FIG. 9, the immune response effects were high in the test groups other than the test groups administered only with low-dose antigens, namely 0.01 µg of the antigen and 0.05 µg of the antigen.

4-3. Conclusion

The H3N2 vaccine composition exhibited variable HI titer and survival rate depending on the presence or absence of the adjuvant at the antigen concentration (0.05 µg) used in the H1N1 test of Example 3. Thus, animal testing for evaluating adjuvant effects of the therapeutic antibodies CT120 and CT149 using the determined H3N2 antigen concentration of 0.05 μg was performed in the same manner as in Example 3, whereby the effects of CT120 and CT149 as the adjuvant for H3N2 vaccine serving as the antigen were confirmed.

Example 5

Mechanism of Adjuvant Function for Influenza Vaccine

Based on the test results of Examples 1 to 4, the therapeutic influenza antibody was concluded to function as an adjuvant for enhancing the effect of the influenza vaccine. Thus, animal testing for the mechanism for generating the adjuvant effect was performed.

The hypothesis about the mechanism for exhibiting the effect of the therapeutic antibody as the adjuvant for influenza vaccine is that the Fc region of the antibody may bind to the Fc receptor present in immune cells, whereby the immune response to influenza vaccine may occur more efficiently.

In order to prove this hypothesis, the antibody concentrations of CT120 (mIgG2a) 0.1 μg and 0.5 μg, which manifested the apparent adjuvant effect in Example 3, were chosen, and intact CT120 (mIgG2a) and Fe-free CT120 (mIgG2a) F(ab')2 in various amounts as shown in Table 11 below were reacted with 0.05 μg of H1N1 vaccine and were then intramuscularly injected to mice, after which the induced immune response was observed.

5-1. Antibody Production Result

As shown in Table 11 below, the CT120 (mIgG2a)-administered group was tested at concentrations of 0.1 μg and 0.5 μg, at which the greatest effects as the H1N1 vaccine adjuvant were shown in Example 3. As for the CT120 (mIgG2a) F(ab')2-administered group, testing was performed in the group in which the same amount was administered as to CT120 (mIgG2a) and in the group in which the amount of CT120 (mIgG2a) F(ab')2 was calculated and administered so as to be identical to the molar ratio with the vaccine at 0.5 μg and 0.1 μg of CT120 (mIgG2a).

TABLE 11

| Group | Ag | Adjuvant | Route | Mouse # |
|---|---|---|---|---|
| Group 1 | PBS | — | i.m. | 10 |
| Group 2 | H1N1 vaccine 0.05 μg | — | i.m. | 10 |
| Group 3 | PBS | CT 120 (mIgG2a) F(ab')2 0.5 μg | i.m. | 10 |
| Group 4 | PBS | CT 120 (mIgG2a) 0.5 μg | i.m. | 10 |
| Group 5 | H1N1 vaccine 0.05 μg | Alum | i.m. | 10 |
| Group 6 | H1N1 vaccine 0.05 μg | CT 120 (mIgG2a) 0.5 μg | i.m. | 10 |
| Group 7 | H1N1 vaccine 0.05 μg | CT 120 (mIgG2a) 0.1 μg | i.m. | 10 |
| Group 8 | H1N1 vaccine 0.05 μg | CT 120 (mIgG2a) F(ab')2 0.5 μg | i.m. | 10 |
| Group 9 | H1N1 vaccine 0.05 μg | CT 120 (mIgG2a) F(ab')2 0.3 μg | i.m. | 10 |
| Group 10 | H1N1 vaccine 0.05 μg | CT 120 (mIgG2a) F(ab')2 0.1 μg | i.m. | 10 |
| Group 11 | H1N1 vaccine 0.05 μg | CT 120 (mIgG2a) F(ab')2 0.06 μg | i.m. | 10 |

H1N1 vaccine was mixed with various concentrations of CT120 (mIgG2a) or CT120 (mIgG2a) F(ab')2, reacted at 37° C. for 1 hr, and intramuscularly injected twice to mice at an interval of 2 weeks as shown in Table 11, after which the immune response induced in each test group was observed. 13 days, 20 days and 27 days after the first intramuscular injection, the serum was sampled in each test group and the antibody titer against H1N1 virus in the serum and the neutralizing antibody titer against H1N1 virus were measured through ELISA and HI, respectively.

As shown in the results of FIG. 10, the antibody titer was relatively low when using CT120 (mIgG2a) F(ab')2, and the antibody titer difference was not significantly different in any of the test groups.

TABLE 12

| Group | Ag | Adjuvant | Route | Mouse # |
|---|---|---|---|---|
| Group 1 | PBS | — | i.m. | N.D. |
| Group 2 | H1N1 vaccine 0.05 μg | — | i.m. | 20 |
| Group 3 | PBS | CT 120 (mIgG2a) F(ab')2 0.5 μg | i.m. | N.D. |
| Group 4 | PBS | CT 120 (mIgG2a) 0.5 μg | i.m. | N.D. |
| Group 5 | H1N1 vaccine 0.05 μg | Alum | i.m. | 160 |
| Group 6 | H1N1 vaccine 0.05 μg | CT 120 (mIgG2a) 0.5 μg | i.m. | 160 |
| Group 7 | H1N1 vaccine 0.05 μg | CT 120 (mIgG2a) 0.1 μg | i.m. | 80 |
| Group 8 | H1N1 vaccine 0.05 μg | CT 120 (mIgG2a) F(ab')2 0.5 μg | i.m. | 40 |
| Group 9 | H1N1 vaccine 0.05 μg | CT 120 (mIgG2a) F(ab')2 0.3 μg | i.m. | 20 |
| Group 10 | H1N1 vaccine 0.05 μg | CT 120 (mIgG2a) F(ab')2 0.1 μg | i.m. | 20 |
| Group 11 | H1N1 vaccine 0.05 μg | CT 120 (mIgG2a) F(ab')2 0.06 μg | i.m. | 40 |

As is apparent from the results of Table 12, the HI titer in all of the test groups using CT120 (mIgG2a) F(ab')2 as the adjuvant (Groups 8 to 11) was similar to that of the test group (Group 2) in which the H1N1 vaccine was administered alone without the adjuvant. In contrast, the test groups (Groups 6 and 7) using intact CT120 (mIgG2a) as the adjuvant exhibited HI titers of 160 and 80, respectively, which are increased 8 times and 4 times compared to the test group in which the H1N1 vaccine was administered alone (Group 2).

5-2. Protective Immunity Result

In order to evaluate the protective immunity against influenza virus, 4 weeks after the second immunization, $10MLD_{50}$ of CA/04/09 H1N1 virus was inoculated to the immunized mouse nasal cavity and allowed to infect it, after which the survival rate of each mouse was measured for 15 days.

TABLE 13

| Group | Ag | Adjuvant | Survival rate (%) |
|---|---|---|---|
| Group 1 | PBS | — | 0% |
| Group 2 | H1N1 vaccine 0.05 µg | — | 20% |
| Group 3 | PBS | CT 120 (mIgG2a) F(ab')2 0.5 µg | 0% |
| Group 4 | PBS | CT 120 (mIgG2a) 0.5 µg | 0% |
| Group 5 | H1N1 vaccine 0.05 µg | Alum | 80% |
| Group 6 | H1N1 vaccine 0.05 µg | CT 120 (mIgG2a) 0.5 µg | 100% |
| Group 7 | H1N1 vaccine 0.05 µg | CT 120 (mIgG2a) 0.1 µg | 90% |
| Group 8 | H1N1 vaccine 0.05 µg | CT 120 (mIgG2a) F(ab')2 0.5 µg | 50% |
| Group 9 | H1N1 vaccine 0.05 µg | CT 120 (mIgG2a) F(ab')2 0.3 µg | 30% |
| Group 10 | H1N1 vaccine 0.05 µg | CT 120 (mIgG2a) F(ab')2 0.1 µg | 30% |
| Group 11 | H1N1 vaccine 0.05 µg | CT 120 (mIgG2a) F(ab')2 0.06 µg | 30% |

As is apparent from the results of Table 13, the test groups using intact CT120 (mIgG2a) as the adjuvant (Groups 6 and 7) exhibited a high survival rate, as in Example 3, but the test groups using CT120 (mIgG2a) F(ab')2 as the adjuvant (Groups 8 to 11) manifested a survival rate similar to that of the test group using only the antigen (Group 2).

5-3. Conclusion

Based on the above results, the Fc region of the antibody was found to play an important role as the influenza vaccine adjuvant.

Example 6

Target Immune Cells Discovery of Influenza Vaccine Adjuvant 6-1. Verification of Target Immune Cells The Fc region of the influenza antibody was confirmed to play an important function as the adjuvant in Example 5. Accordingly, animal testing was performed to discover cells having an immune response varying depending on the binding to the Fc region, among immune cells that express the Fc receptor. Used as the amount of the antibody was mouse-form CT120 (mIgG2a) 0.5 µg, which exhibited the greatest effect as the H1N1 vaccine adjuvant in Example 3.

TABLE 14

| Group | Ag | Adjuvant | Route | Mouse # |
|---|---|---|---|---|
| Group 1 | PBS | — | i.m | 3 |
| Group 2 | H1N1 vaccine 0.05 µg | — | i.m | 3 |
| Group 3 | — | CT 120 (mIgG2a) 0.5 µg | i.m | 3 |
| Group 4 | H1N1 vaccine 0.05 µg | Alum | i.m | 3 |
| Group 5 | H1N1 vaccine 0.05 µg | CT 120 (mIgG2a) 0.5 µg | i.m | 3 |
| Group 6 | H1N1 vaccine 0.05 µg | CT 120 (mIgG2a) F(ab') 2 0.5 µg | i.m | 3 |

The H1N1 vaccine and the adjuvant were mixed, reacted at 37° C. for 1 hr, and intramuscularly injected twice to mice at an interval of 2 weeks, as set forth in Table 14. 1 day, 3 days and 7 days thereafter, the spleen and the inguinal lymph node in each mouse were separated and thus the number of various immune cells and the corresponding cell proportion were measured.

Figure 11:
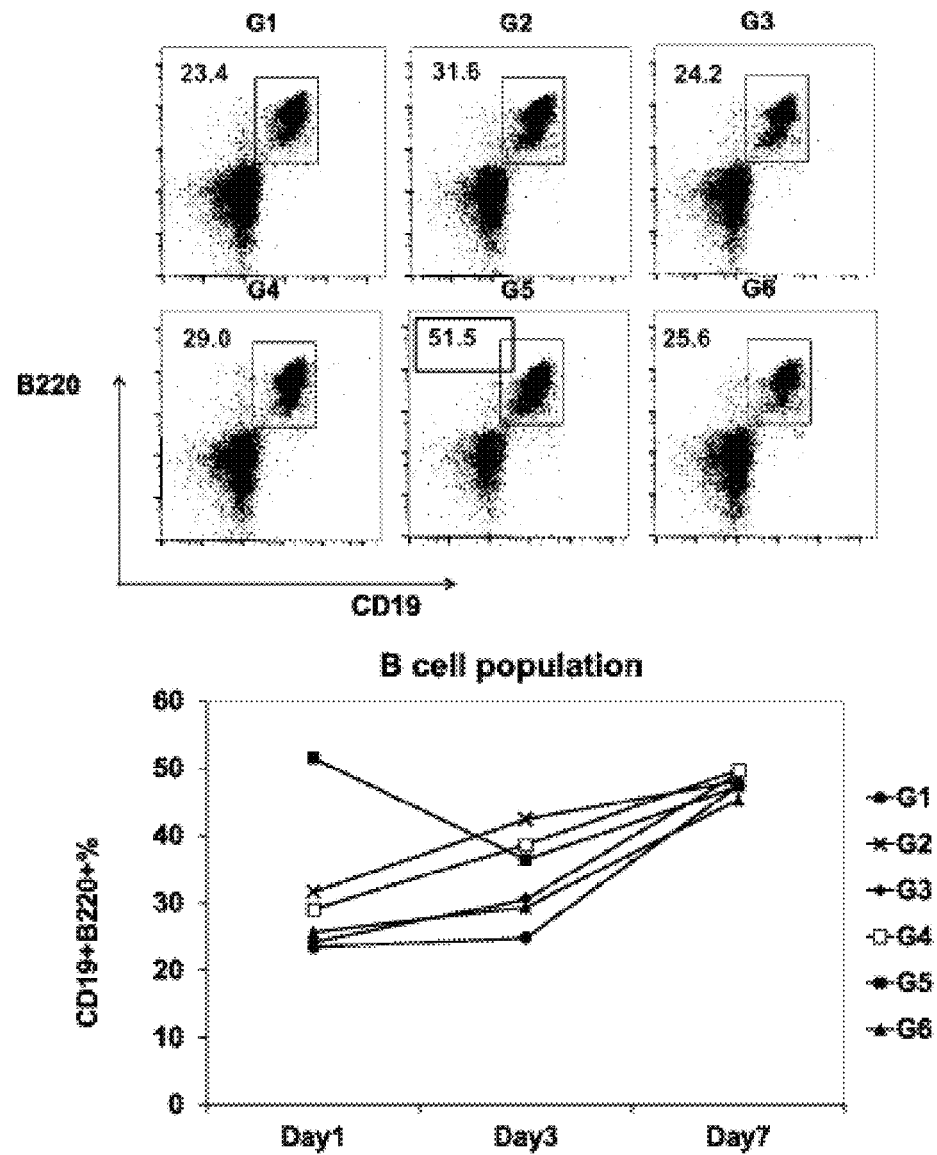
Figure 12:
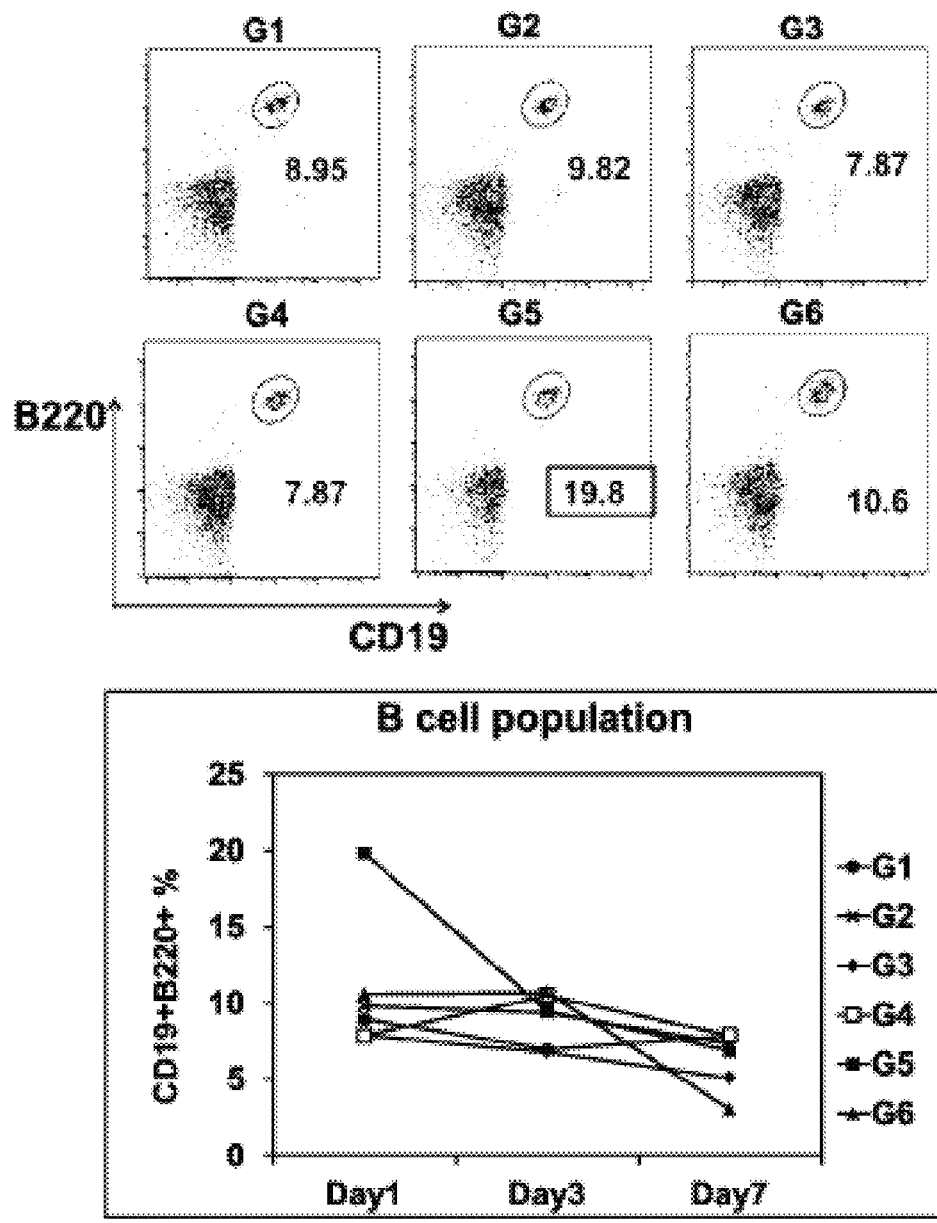

As shown in the results of FIGS. 11 and 12, when H1N1 vaccine and CT120 (mIgG2a) were added, the amount of B cells was approximately doubled in both the spleen and the inguinal lymph node 1 day after the two intramuscular injections, compared to the other administered groups. On the $3^{rd}$ day and the $7^{th}$ day, relatively similar cell proportion resulted.

Thus, the CT120 adjuvant was confirmed to increase the immune response of B cells through the Fc region. In the CT120 F(ab')2-administered group, there was no difference with the mouse to which the PBS control was administered, and thus the importance of the Fc region was confirmed once more. Accordingly, the CT120 adjuvant can be found to increase the immunogenicity of the H1N1 vaccine through a mechanism different from that of the commercially available adjuvant Alum.

6-2. Protective Immunity Result of B Cells

The CT120 adjuvant was confirmed to enhance B cell immunity in Example 6-1. Based thereon, animal testing for evaluating whether the CT120 adjuvant is able to be associated with the protective immunity of B cells even in a state of viral inoculation was performed.

TABLE 15

| Group | Ag | Adjuvant | Route | Mouse # |
|---|---|---|---|---|
| Group 1 | PBS | — | i.m | 3 |
| Group 2 | H1N1 vaccine 0.05 µg | — | i.m | 3 |
| Group 3 | H1N1 vaccine 0.05 µg | CT 120 (mIgG2a) 0.5 µg | i.m | 3 |
| Group 4 | H1N1 vaccine 0.05 µg | Alum | i.m | 3 |

As set forth in Table 15, the H1N1 vaccine composition was intramuscularly injected twice to mice at an interval of 2 weeks. After 4 weeks, $10MLD_{50}$ of CA/04/09 H1N1 virus was inoculated to the immunized mouse nasal cavity. 1 day and 3 days after viral infection, the spleen and the internal lymph node in each mouse were separated and the B cell proportion in all the cells was measured using a flow cytometer.

Figure 13:
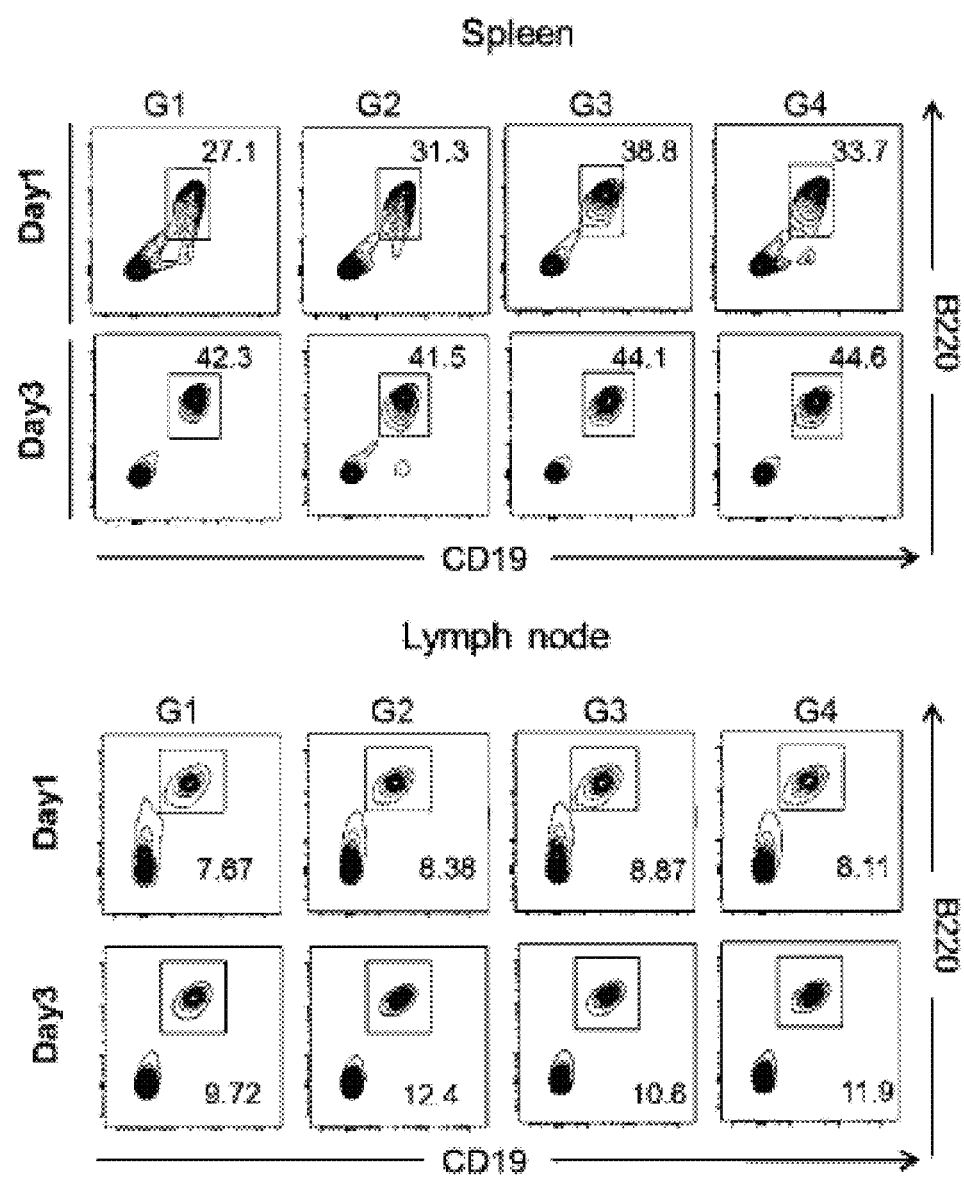

As seen in the results of FIG. 13, when the spleen was analyzed 1 day after viral infection, the B cell population was increased by about 10% in the test group using both the H1N1 vaccine and CT120 compared to the PBS control. In the test group using both the vaccine and Alum, the B cell population was significantly increased compared to the PBS control, but was not greatly increased compared to the test group using CT120. Furthermore, immature B cells, namely B-1 cells (CD19+B220−) were present in the other groups, but only B-2 cells (CD19+B220+) developed from the B-1 cells were present in the test group using the H1N1 vaccine and CT120. In the case of lymph nodes, as in the spleen, the B cell proportion was not drastically increased, but was significantly increased in three repeated experiments.

6-3. Conclusion

Thereby, when CT120 was used as the adjuvant, more mature B cells were rapidly formed.

Example 7

Comparison of Effects of Commercially Available Adjuvant and CT120

Through the above Example, CT120 was confirmed to be effective as the influenza vaccine adjuvant, and this effect was compared with the effect of a currently useful influenza vaccine adjuvant. The currently commercially available seasonal influenza vaccine adjuvant is MF59, Fluad of Novartis. In the following comparison test, AddaVax™ (InvivoGen, Catalog # vac-adx-10) having the same composition as MF59 was used.

7-1. Antibody Production Result

Testing was performed using 0.5 μg and 0.1 μg of mouse-form CT120 (mIgG2a), showing the greatest effect as the H1N1 vaccine adjuvant in Example 3. In Table 16 below, 100% AddaVax indicates the amount of the adjuvant contained in 45 μg of seasonal influenza vaccine HA.

TABLE 16

| Group | Ag | Adjuvant | Route | Mouse # |
|---|---|---|---|---|
| Group 1 | PBS | — | i.m. | 10 |
| Group 2 | H1N1 vaccine 0.05 μg | — | i.m. | 10 |
| Group 3 | PBS | CT 120 (mIgG2a) Fab 0.5 μg | i.m. | 10 |
| Group 4 | PBS | AddaVax 100% | i.m. | 10 |
| Group 5 | H1N1 vaccine 0.05 μg | Alum | i.m. | 10 |
| Group 6 | H1N1 vaccine 0.05 μg | CT 120 (mIgG2a) 0.5 μg | i.m. | 10 |
| Group 7 | H1N1 vaccine 0.05 μg | CT 120 (mIgG2a) 0.1 μg | i.m. | 10 |
| Group 8 | H1N1 vaccine 0.05 μg | AddaVax 100% | i.m. | 10 |
| Group 9 | H1N1 vaccine 0.05 μg | AddaVax 10% | i.m. | 10 |
| Group 10 | H1N1 vaccine 0.05 μg | AddaVax 1% | i.m. | 10 |

H1N1 vaccine was mixed with CT120 (mIgG2a) or AddaVax having the same composition as the commercially available adjuvant, reacted at 37° C. for 1 hr, and intramuscularly injected twice to mice at an interval of 2 weeks, as set forth in Table 16, and the immune response induced in each test group was then observed. 13 days, 20 days and 27 days after the first intramuscular injection, the serum was sampled in each test group and the antibody titer against H1N1 virus in the serum and the neutralizing antibody titer against H1N1 virus were measured through ELISA and HI, respectively.

Figure 14:
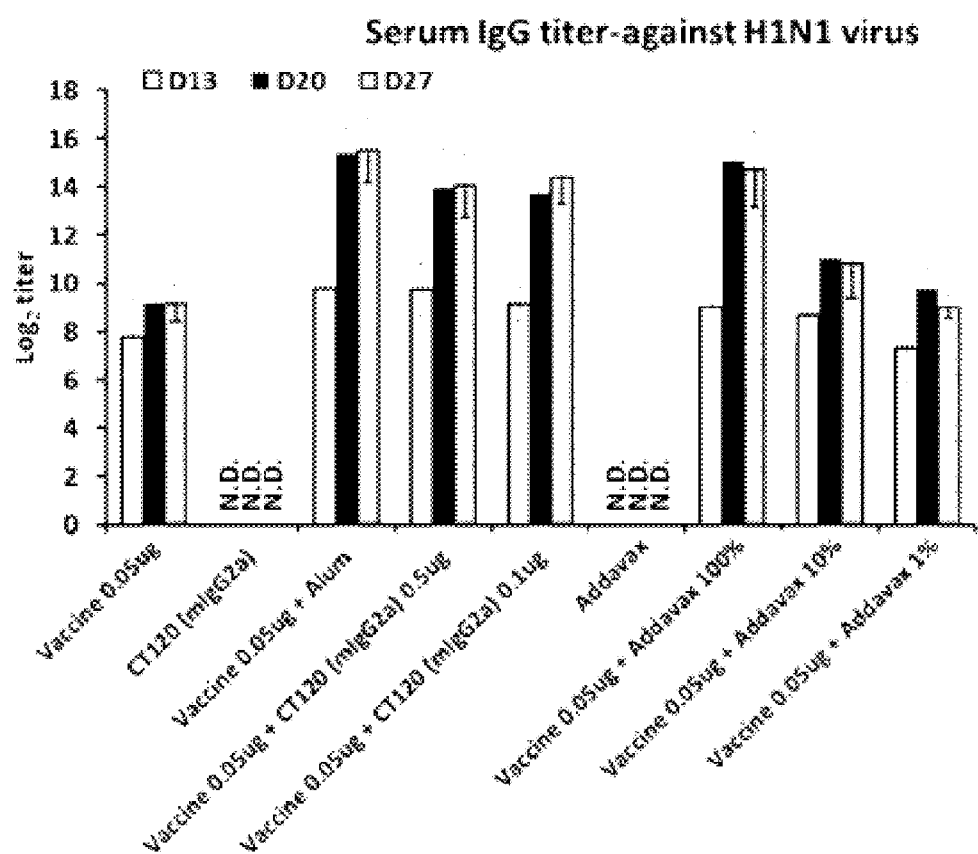

As seen in the results of FIG. 14, only the test group administered with 100% AddaVax exhibited the antibody titer similar to that of the test groups administered with 0.5 μg and 0.1 μg of CT120 (mIgG2a). When 10% and 1% AddaVax were administered, low antibody titers resulted.

TABLE 17

| Group | Ag | Adjuvant | HI titer |
|---|---|---|---|
| Group 1 | PBS | — | N.D. |
| Group 2 | H1N1 vaccine 0.05 μg | — | 20 |
| Group 3 | PBS | CT 120 (mIgG2a) Fab 0.5 μg | N.D. |
| Group 4 | PBS | AddaVax 100% | N.D. |
| Group 5 | H1N1 vaccine 0.05 μg | Alum | 160 |
| Group 6 | H1N1 vaccine 0.05 μg | CT 120 (mIgG2a) 0.5 μg | 160 |
| Group 7 | H1N1 vaccine 0.05 μg | CT 120 (mIgG2a) 0.1 μg | 80 |
| Group 8 | H1N1 vaccine 0.05 μg | AddaVax 100% | 160 |
| Group 9 | H1N1 vaccine 0.05 μg | AddaVax 10% | 20 |
| Group 10 | H1N1 vaccine 0.05 μg | AddaVax 1% | N.D. |

As is apparent from the results of Table 17, the 100% AddaVax-administered test group (Group 8) exhibited the HI titer similar to the test groups administered with 0.5 μg and 0.1 μg of CT120 (mIgG2a) (Groups 6 and 7), but the test groups administered with 1% and 10% AddaVax (Groups 10 and 9) manifested the HI titer similar to the test group administered only with H1N1 vaccine (Group 2) or the HI titer thereof was not measured.

7-2. Protective Immunity Result

In order to evaluate the protective immunity against influenza virus, 4 weeks after the second immunization, 10MLD$_{50}$ of CA/04/09 H1N1 virus was inoculated to the immunized mouse nasal cavity and allowed to infect it, after which the mouse survival rate was measured for 15 days.

TABLE 18

| Group | Ag | Adjuvant | Survival rate (%) |
|---|---|---|---|
| Group 1 | PBS | — | 0 |
| Group 2 | H1N1 vaccine 0.05 μg | — | 20 |
| Group 3 | PBS | CT 120 (mIgG2a) Fab 0.5 μg | 0 |
| Group 4 | PBS | AddaVax 100% | 0 |
| Group 5 | H1N1 vaccine 0.05 μg | Alum | 80 |
| Group 6 | H1N1 vaccine 0.05 μg | CT 120 (mIgG2a) 0.5 μg | 100 |
| Group 7 | H1N1 vaccine 0.05 μg | CT 120 (mIgG2a) 0.1 μg | 90 |
| Group 8 | H1N1 vaccine 0.05 μg | AddaVax 100% | 90 |
| Group 9 | H1N1 vaccine 0.05 μg | AddaVax 10% | 60 |
| Group 10 | H1N1 vaccine 0.05 μg | AddaVax 1% | 0 |

As is apparent from the results of Table 18, the test group administered with 100% AddaVax (Group 8) exhibited a survival rate similar to that of the test groups administered with 0.5 μg and 0.1 μg of CT120 (mIgG2a) (Groups 6 and 7), and the survival rate was decreased in the test groups administered with 1% and 10% AddaVax (Groups 10 and 9).

7-3. Conclusion

Therefore, the adjuvant effect when H1N1 vaccine was added with 0.5 μg and 0.1 μg of CT120 (mIgG2a) was similar to the effect when the adjuvant was added in an amount (100% AddaVax) in 45 μg of the commercially available influenza vaccine HA. In Example 4, when 0.5 μg of CT149 (mIgG2a) was used as the adjuvant, similar results were obtained compared to when 0.1 μg and 0.5 μg of CT120 (mIgG2a) were administered, from which CT149 (mIgG2a) can be expected to exhibit effects similar to those of CT120 (mIgG2a).

The invention claimed is:

1. A method of enhancing an immune response to an influenza A virus in a subject which comprises administering to the subject a vaccine composition comprising a complex of the influenza A virus and an antibody directed to the influenza A virus,
   wherein the ratio by weight of the influenza A virus to the antibody directed to the influenza A virus in the complex is between 1:1 and 1:10,
   wherein the antibody directed to the influenza A virus binds to one epitope selected from the group consisting of:
   i) an epitope comprising an amino acid residue at positions 18, 38, 40, 291, 292 and 318 of an HA1 polypeptide; and amino acid residues at positions 18, 19, 20, 21, 41, 42, 45, 48, 49, 52 and 53 of an HA2 polypeptide; and
   ii) an epitope comprising an amino acid residue at positions 278 and 318 of an HA1 polypeptide; and amino acid residues at positions 38, 39, 41, 42, 45, 48, 49, 52 and 53 of an HA2 polypeptide.

2. The method of claim 1, wherein the antibody is specifically bound to the influenza A virus and the complex binds to an Fc receptor of immune cells.

3. The method of claim 1, wherein the antibody directed to the influenza A virus is selected from the group consisting of i) an antibody comprising a light-chain variable domain including a CDR1 region the sequence of which is set forth in SEQ ID NO:1, a CDR2 region the sequence of which is set forth in SEQ ID NO:2 and a CDR3 region the sequence of which is set forth in SEQ ID NO:3, and a heavy-chain variable domain including a CDR1 region the sequence of which is set forth in SEQ ID NO:4, a CDR2 region the sequence of which is set forth in SEQ ID NO:5 and a CDR3 region the sequence of which is set forth in SEQ ID NO:6, as determined according to the Kabat method; and ii) an antibody comprising a light-chain variable domain including a CDR1 region the sequence of which is set forth in SEQ ID NO:7, a CDR2 region the sequence of which is set forth in SEQ ID NO:8 and a CDR3 region the sequence of which is set forth in SEQ ID NO:9, and a heavy-chain variable domain including a CDR1 region the sequence of which is set forth in SEQ ID NO:10, a CDR2 region the sequence of which is set forth in SEQ ID NO:11 and a CDR3 region the sequence of which is set forth in SEQ ID NO:12, as determined according to the Kabat method.

4. The method of claim 1, wherein the antibody directed to the influenza A virus is selected from the group consisting of i) an antibody including a light chain comprising a polypeptide the sequence of which is set forth in SEQ ID NO:13 and a heavy chain comprising a polypeptide the sequence of which is set forth in SEQ ID NO:14; and ii) an antibody including a light chain comprising a polypeptide the sequence of which is set forth in SEQ ID NO:15 and a heavy chain comprising a polypeptide the sequence of which is set forth in SEQ ID NO:16.

* * * * *